(12) United States Patent
Klee et al.

(10) Patent No.: US 8,273,539 B2
(45) Date of Patent: Sep. 25, 2012

(54) EXTRACELLULAR AND MEMBRANE-ASSOCIATED PROSTATE CANCER MARKERS

(75) Inventors: George G. Klee, Rochester, MN (US); George Vasmatzis, Byron, MN (US); Farhad Kosari, Rochester, MN (US); Eric W. Klee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 318 days.

(21) Appl. No.: 12/442,685

(22) PCT Filed: Sep. 25, 2007

(86) PCT No.: PCT/US2007/079423
§ 371 (c)(1),
(2), (4) Date: Mar. 24, 2009

(87) PCT Pub. No.: WO2008/039774
PCT Pub. Date: Apr. 3, 2008

(65) Prior Publication Data
US 2010/0028881 A1  Feb. 4, 2010

Related U.S. Application Data

(60) Provisional application No. 60/847,057, filed on Sep. 25, 2006.

(51) Int. Cl.
*G01N 33/53* (2006.01)
(52) U.S. Cl. ......................................... 435/7.1
(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. | |
| 5,744,305 A | 4/1998 | Fodor et al. | |
| 6,630,358 B1 | 10/2003 | Wagner et al. | |
| 2003/0119168 A1 | 6/2003 | Madison et al. | |
| 2007/0212702 A1 | 9/2007 | Tomlins et al. | |
| 2007/0275915 A1 | 11/2007 | Hallenbeck et al. | |
| 2009/0036415 A1 | 2/2009 | Rubin et al. | |
| 2009/0239221 A1 | 9/2009 | Chinnaiyan et al. | |
| 2010/0257617 A1 | 10/2010 | Arul et al. | |

FOREIGN PATENT DOCUMENTS

| | | |
|---|---|---|
| WO | WO 2008/023087 | 2/2008 |
| WO | WO 2009/009432 | 1/2009 |
| WO | WO 2009/020521 | 2/2009 |

OTHER PUBLICATIONS

Tockman et al (Cancer Res., 1992, 52:2711s-2718s).*
Alberts et al. (Molecular Biology of the Cell, 3rd edition, 1994, p. 465).*
Greenbaum et al. (Genome Biology, 2003, vol. 4, Issue 9, pages 117.1-117.8).*
Pereira et al (Gut, 1992, 33: 98-102).*
Henrotin et al (Biorheology, 2004, 41 (3-4): Abstract).*
Varambally et al., "Integrative Genomic and Proteomic Analysis of Prostate Cancer Reveals Signatures of Metastatic Progression," *Cancer Cell*, 2005, 8(5):393-406.
Authorized Officer Kyu Jeong Ahn, International Search Report/Written Opinion in PCT/US2007/079423 mailed Feb. 27, 2008, 12 pages.
Authorized Officer Beate Giffo-Schmitt, International Preliminary Report on Patentability in PCT/US2007/079423 mailed Apr. 9, 2009, 6 pages.
Klee Eric W., et al., "Candidate Serum Biomarkers for Prostate Adenocarcinoma Identified by mRNA Differences in Prostate Tissue and Verified with Protein Measurements in Tissue and Blood," *Clinical Chemistry*, 58(3): 599-609 (2012).

* cited by examiner

*Primary Examiner* — Sean Aeder
(74) *Attorney, Agent, or Firm* — Fish & Richardson P.C.

(57) ABSTRACT

This document relates to methods and materials involved in identifying, assessing, and monitoring prostate cancer in male mammals. For example, this document provides arrays for detecting polypeptides or nucleic acids that can be used to identify prostate cancer in male mammals. In addition, methods and materials for assessing and monitoring prostate cancer in mammals are provided herein.

3 Claims, No Drawings

SEQUENCE LISTING

<160> NUMBER OF SEQ ID NOS: 63

<210> SEQ ID NO 1
<211> LENGTH: 13
<212> TYPE: PRT
<213> ORGANISM: Homo sapiens

<400> SEQUENCE: 1

Ser Tyr Asp Leu Asp Pro Gly Ala Gly Ser Leu Glu Ile
 1               5                  10

<210> SEQ ID NO 2
<211> LENGTH: 10
<212> TYPE: PRT
<213> ORGANISM: Homo sapiens

<400> SEQUENCE: 2

Ile Gln Asp Ile Asn Asp Asn Glu Pro Lys
 1               5                  10

<210> SEQ ID NO 3
<211> LENGTH: 18
<212> TYPE: PRT
<213> ORGANISM: Homo sapiens

<400> SEQUENCE: 3

Gly Glu Gln Gly Pro Pro Gly Ile Pro Gly Pro Gln Gly Leu Pro Gly
 1               5                  10                  15

Val Lys

<210> SEQ ID NO 4
<211> LENGTH: 13
<212> TYPE: PRT
<213> ORGANISM: Homo sapiens

<400> SEQUENCE: 4

Glu Leu Gln Glu Thr Asn Ala Ala Leu Gln Asp Val Arg
 1               5                  10

<210> SEQ ID NO 5
<211> LENGTH: 12
<212> TYPE: PRT
<213> ORGANISM: Homo sapiens

<400> SEQUENCE: 5

Leu Val Pro Asn Pro Gly Gln Glu Asp Ala Asp Arg
 1               5                  10

<210> SEQ ID NO 6
<211> LENGTH: 13
<212> TYPE: PRT
<213> ORGANISM: Homo sapiens

<400> SEQUENCE: 6

Asn Gln Gly Thr Ser Asp Phe Leu Pro Ser Arg Pro Arg
 1               5                  10

<210> SEQ ID NO 7
<211> LENGTH: 10
<212> TYPE: PRT
<213> ORGANISM: Homo sapiens

<400> SEQUENCE: 7

```
Glu Pro Pro Ala Ala Pro Gly Ala Trp Arg
 1               5                  10

<210> SEQ ID NO 8
<211> LENGTH: 10
<212> TYPE: PRT
<213> ORGANISM: Homo sapiens

<400> SEQUENCE: 8

Val Ala Glu Asn Glu Asn Pro Gly Ala Arg
 1               5                  10

<210> SEQ ID NO 9
<211> LENGTH: 18
<212> TYPE: PRT
<213> ORGANISM: Homo sapiens

<400> SEQUENCE: 9

Gly Ala Asn Gly Asp Pro Gly Arg Pro Gly Glu Pro Gly Leu Pro Gly
 1               5                  10                  15

Ala Arg

<210> SEQ ID NO 10
<211> LENGTH: 16
<212> TYPE: PRT
<213> ORGANISM: Homo sapiens

<400> SEQUENCE: 10

Ala Gly Glu Pro Gly Leu Gln Gly Pro Ala Gly Pro Pro Gly Glu Lys
 1               5                  10                  15

<210> SEQ ID NO 11
<211> LENGTH: 15
<212> TYPE: PRT
<213> ORGANISM: Homo sapiens

<400> SEQUENCE: 11

Gly Pro Pro Gly Pro Gln Gly Pro Ala Gly Glu Gln Gly Pro Arg
 1               5                  10                  15

<210> SEQ ID NO 12
<211> LENGTH: 19
<212> TYPE: PRT
<213> ORGANISM: Homo sapiens

<400> SEQUENCE: 12

Ala Gly Pro Asp Gly Pro Asp Gly Lys Pro Gly Ile Asp Gly Leu Thr
 1               5                  10                  15

Gly Ala Lys

<210> SEQ ID NO 13
<211> LENGTH: 15
<212> TYPE: PRT
<213> ORGANISM: Homo sapiens

<400> SEQUENCE: 13

Gly Ile Leu Gly Asp Pro Gly His Gln Gly Lys Pro Gly Pro Lys
 1               5                  10                  15

<210> SEQ ID NO 14
<211> LENGTH: 17
<212> TYPE: PRT
<213> ORGANISM: Homo sapiens

<400> SEQUENCE: 14
```

```
Ala Thr Asp Pro Asp Glu Gly Ala Asn Gly Asp Val Thr Tyr Ser Phe
 1               5                  10                  15

Arg

<210> SEQ ID NO 15
<211> LENGTH: 12
<212> TYPE: PRT
<213> ORGANISM: Homo sapiens

<400> SEQUENCE: 15

His Leu Thr Pro Val Thr Leu Glu Leu Gly Gly Lys
 1               5                  10

<210> SEQ ID NO 16
<211> LENGTH: 14
<212> TYPE: PRT
<213> ORGANISM: Homo sapiens

<400> SEQUENCE: 16

Ser Gly Val Gln Gln Leu Ile Gln Tyr Tyr Gln Asp Gln Lys
 1               5                  10

<210> SEQ ID NO 17
<211> LENGTH: 17
<212> TYPE: PRT
<213> ORGANISM: Homo sapiens

<400> SEQUENCE: 17

Leu Tyr Leu Ser His Asn Gln Leu Ser Glu Ile Pro Leu Asn Leu Pro
 1               5                  10                  15

Lys

<210> SEQ ID NO 18
<211> LENGTH: 19
<212> TYPE: PRT
<213> ORGANISM: Homo sapiens

<400> SEQUENCE: 18

Ala Leu Glu Ile Leu Gln Glu Glu Asp Leu Ile Asp Glu Asp Asp Ile
 1               5                  10                  15

Pro Val Arg

<210> SEQ ID NO 19
<211> LENGTH: 19
<212> TYPE: PRT
<213> ORGANISM: Homo sapiens

<400> SEQUENCE: 19

Ala Leu Glu Ile Leu Gln Glu Glu Asp Leu Ile Asp Glu Asp Asp Ile
 1               5                  10                  15

Pro Val Arg

<210> SEQ ID NO 20
<211> LENGTH: 17
<212> TYPE: PRT
<213> ORGANISM: Homo sapiens

<400> SEQUENCE: 20

Gly His Leu Phe Leu Gln Thr Asp Gln Pro Ile Tyr Asn Pro Gly Gln
 1               5                  10                  15

Arg
```

```
<210> SEQ ID NO 21
<211> LENGTH: 13
<212> TYPE: PRT
<213> ORGANISM: Homo sapiens

<400> SEQUENCE: 21

Gly Leu Glu Glu Glu Leu Gln Phe Ser Leu Gly Ser Lys
 1               5                  10

<210> SEQ ID NO 22
<211> LENGTH: 19
<212> TYPE: PRT
<213> ORGANISM: Homo sapiens

<400> SEQUENCE: 22

Asn Tyr Tyr Ile Ala Ala Glu Glu Ile Ser Trp Asp Tyr Ser Glu Phe
 1               5                  10                  15

Val Gln Arg

<210> SEQ ID NO 23
<211> LENGTH: 14
<212> TYPE: PRT
<213> ORGANISM: Homo sapiens

<400> SEQUENCE: 23

Ser Tyr Thr Ile His Tyr Ser Glu Gln Gly Val Glu Trp Lys
 1               5                  10

<210> SEQ ID NO 24
<211> LENGTH: 19
<212> TYPE: PRT
<213> ORGANISM: Homo sapiens

<400> SEQUENCE: 24

Asp Gly Leu Asp Ile Gln Leu Pro Gly Asp Asp Pro His Ile Ser Val
 1               5                  10                  15

Gln Phe Arg

<210> SEQ ID NO 25
<211> LENGTH: 11
<212> TYPE: PRT
<213> ORGANISM: Homo sapiens

<400> SEQUENCE: 25

His His Val Leu His Asp Gln Glu Val Asp Arg
 1               5                  10

<210> SEQ ID NO 26
<211> LENGTH: 17
<212> TYPE: PRT
<213> ORGANISM: Homo sapiens

<400> SEQUENCE: 26

Gln Tyr Leu Leu Leu Asp Ser His Thr Gly Asn Leu Leu Thr Asn Glu
 1               5                  10                  15

Lys

<210> SEQ ID NO 27
<211> LENGTH: 12
<212> TYPE: PRT
<213> ORGANISM: Homo sapiens

<400> SEQUENCE: 27
```

```
Asp Ile Asn Asp His Ala Pro Val Phe Gln Asp Lys
 1               5                  10

<210> SEQ ID NO 28
<211> LENGTH: 21
<212> TYPE: PRT
<213> ORGANISM: Homo sapiens

<400> SEQUENCE: 28

Ile Leu Glu Asp Gln Glu Glu Asn Pro Leu Pro Ala Ala Leu Val Gln
 1               5                  10                  15

Pro His Thr Gly Lys
            20

<210> SEQ ID NO 29
<211> LENGTH: 24
<212> TYPE: PRT
<213> ORGANISM: Homo sapiens

<400> SEQUENCE: 29

Phe Asn Leu Asp Leu Thr His Pro Val Glu Asp Gly Ile Phe Asp Ser
 1               5                  10                  15

Gly Asn Phe Glu Gln Phe Leu Arg
            20

<210> SEQ ID NO 30
<211> LENGTH: 9
<212> TYPE: PRT
<213> ORGANISM: Homo sapiens

<400> SEQUENCE: 30

Tyr Glu Ala Ala Val Pro Asp Pro Arg
 1               5

<210> SEQ ID NO 31
<211> LENGTH: 11
<212> TYPE: PRT
<213> ORGANISM: Homo sapiens

<400> SEQUENCE: 31

Glu Thr Gly Leu Glu Thr Ser Ser Gly Gly Lys
 1               5                  10

<210> SEQ ID NO 32
<211> LENGTH: 11
<212> TYPE: PRT
<213> ORGANISM: Homo sapiens

<400> SEQUENCE: 32

Asp Ile Ile Pro Glu Thr Leu Phe Ile Pro Arg
 1               5                  10

<210> SEQ ID NO 33
<211> LENGTH: 11
<212> TYPE: PRT
<213> ORGANISM: Homo sapiens

<400> SEQUENCE: 33

Val Glu Ala Glu Asn Thr His Val Asp Pro Arg
 1               5                  10

<210> SEQ ID NO 34
<211> LENGTH: 10
<212> TYPE: PRT
<213> ORGANISM: Homo sapiens
```

<400> SEQUENCE: 34

Ser Ser His Pro Glu Thr Tyr Gln Gln Arg
1               5                   10

<210> SEQ ID NO 35
<211> LENGTH: 9
<212> TYPE: PRT
<213> ORGANISM: Homo sapiens

<400> SEQUENCE: 35

Thr Val Glu Ser Leu Pro Asn Leu Arg
1               5

<210> SEQ ID NO 36
<211> LENGTH: 11
<212> TYPE: PRT
<213> ORGANISM: Homo sapiens

<400> SEQUENCE: 36

Ile Asp Asn Pro His Ile Thr Tyr Thr Ala Arg
1               5                   10

<210> SEQ ID NO 37
<211> LENGTH: 10
<212> TYPE: PRT
<213> ORGANISM: Homo sapiens

<400> SEQUENCE: 37

Gly Thr Thr Gly Thr Gln Leu Asn Gly Arg
1               5                   10

<210> SEQ ID NO 38
<211> LENGTH: 7
<212> TYPE: PRT
<213> ORGANISM: Homo sapiens

<400> SEQUENCE: 38

Trp Leu Gln Gln Glu Val Lys
1               5

<210> SEQ ID NO 39
<211> LENGTH: 17
<212> TYPE: PRT
<213> ORGANISM: Homo sapiens

<400> SEQUENCE: 39

Ala Glu Gly Gln Trp Thr Leu Glu Ile Gln Asp Leu Pro Ser Gln Val
1               5                   10                  15

Arg

<210> SEQ ID NO 40
<211> LENGTH: 13
<212> TYPE: PRT
<213> ORGANISM: Homo sapiens

<400> SEQUENCE: 40

Gly Leu Pro Trp Gln Ser Ser Asp Gln Asp Ile Ala Arg
1               5                   10

<210> SEQ ID NO 41
<211> LENGTH: 17
<212> TYPE: PRT
<213> ORGANISM: Homo sapiens

```
<400> SEQUENCE: 41

Asp Lys Leu Arg Lys Glu Ser Lys Asn Leu Asn Ile Gln Gly Ser Lys
1               5                   10                  15

Phe

<210> SEQ ID NO 42
<211> LENGTH: 11
<212> TYPE: PRT
<213> ORGANISM: Homo sapiens

<400> SEQUENCE: 42

Ile Glu Ala Leu Ser Ser Ala Leu Gln Ile Phe
1               5                   10

<210> SEQ ID NO 43
<211> LENGTH: 16
<212> TYPE: PRT
<213> ORGANISM: Homo sapiens

<400> SEQUENCE: 43

Leu Gly Ser Pro Leu Arg Gly Gly Ser Ser Leu Arg His Val Val Tyr
1               5                   10                  15

<210> SEQ ID NO 44
<211> LENGTH: 12
<212> TYPE: PRT
<213> ORGANISM: Homo sapiens

<400> SEQUENCE: 44

Leu Ser Glu Pro Ala Glu Leu Thr Asp Ala Val Lys
1               5                   10

<210> SEQ ID NO 45
<211> LENGTH: 12
<212> TYPE: PRT
<213> ORGANISM: Homo sapiens

<400> SEQUENCE: 45

His Ser Gln Pro Trp Gln Val Leu Val Ala Ser Arg
1               5                   10

<210> SEQ ID NO 46
<211> LENGTH: 9
<212> TYPE: PRT
<213> ORGANISM: Homo sapiens

<400> SEQUENCE: 46

Glu Thr His Ala Ser Ala Pro Val Lys
1               5

<210> SEQ ID NO 47
<211> LENGTH: 13
<212> TYPE: PRT
<213> ORGANISM: Homo sapiens

<400> SEQUENCE: 47

Gly Leu Gly Ala Thr Thr His Pro Thr Ala Ala Val Lys
1               5                   10

<210> SEQ ID NO 48
<211> LENGTH: 13
<212> TYPE: PRT
<213> ORGANISM: Homo sapiens

<400> SEQUENCE: 48
```

```
Gln Leu Cys Ala Pro Pro Asp Gln Pro Trp Val Glu Arg
1               5                   10
```

<210> SEQ ID NO 49
<211> LENGTH: 16
<212> TYPE: PRT
<213> ORGANISM: Homo sapiens

<400> SEQUENCE: 49

```
Glu Ile Pro Ala Trp Val Pro Glu Asp Pro Ala Ala Gln Ile Thr Lys
1               5                   10                  15
```

<210> SEQ ID NO 50
<211> LENGTH: 10
<212> TYPE: PRT
<213> ORGANISM: Homo sapiens

<400> SEQUENCE: 50

```
Thr Pro Asp Val Ser Ser Ala Leu Asp Lys
1               5                   10
```

<210> SEQ ID NO 51
<211> LENGTH: 14
<212> TYPE: PRT
<213> ORGANISM: Homo sapiens

<400> SEQUENCE: 51

```
Thr Thr Asn Ile Gln Gly Ile Asn Leu Leu Phe Ser Ser Arg
1               5                   10
```

<210> SEQ ID NO 52
<211> LENGTH: 16
<212> TYPE: PRT
<213> ORGANISM: Homo sapiens

<400> SEQUENCE: 52

```
Glu Ile Pro Ala Trp Val Pro Phe Asp Pro Ala Ala Gln Ile Thr Lys
1               5                   10                  15
```

<210> SEQ ID NO 53
<211> LENGTH: 16
<212> TYPE: PRT
<213> ORGANISM: Homo sapiens

<400> SEQUENCE: 53

```
Glu Leu Pro Ala Ala Val Ala Pro Ala Gly Pro Ala Ser Leu Ala Arg
1               5                   10                  15
```

<210> SEQ ID NO 54
<211> LENGTH: 21
<212> TYPE: PRT
<213> ORGANISM: Homo sapiens

<400> SEQUENCE: 54

```
Pro Leu Pro Glu Pro Leu Thr Val Gln Leu Leu Thr Val Pro Gly Glu
1               5                   10                  15

Val Phe Pro Pro Lys
            20
```

<210> SEQ ID NO 55
<211> LENGTH: 12
<212> TYPE: PRT
<213> ORGANISM: Homo sapiens

<400> SEQUENCE: 55

Val Ala Ile Gly Gly Gln Ser Asn Glu Ser Asp Arg
1               5                   10

<210> SEQ ID NO 56
<211> LENGTH: 11
<212> TYPE: PRT
<213> ORGANISM: Homo sapiens

<400> SEQUENCE: 56

Leu Leu Pro Ala Leu Gln Ser Thr Ile Thr Arg
1               5                   10

<210> SEQ ID NO 57
<211> LENGTH: 15
<212> TYPE: PRT
<213> ORGANISM: Homo sapiens

<400> SEQUENCE: 57

Gln Gly Gly Val Asn Ala Thr Gln Val Leu Ile Gln His Leu Arg
1               5                   10                  15

<210> SEQ ID NO 58
<211> LENGTH: 13
<212> TYPE: PRT
<213> ORGANISM: Homo sapiens

<400> SEQUENCE: 58

Leu Glu Gly His Gly Asp Pro Leu His Glu Glu Val Lys
1               5                   10

<210> SEQ ID NO 59
<211> LENGTH: 12
<212> TYPE: PRT
<213> ORGANISM: Homo sapiens

<400> SEQUENCE: 59

Asp Leu Gly Leu Ala Glu Gly Glu Leu Ala Ala Arg
1               5                   10

<210> SEQ ID NO 60
<211> LENGTH: 14
<212> TYPE: PRT
<213> ORGANISM: Homo sapiens

<400> SEQUENCE: 60

Ser Ile Leu Gln Gly Gln Pro Tyr Phe Ser Val Glu Pro Lys
1               5                   10

<210> SEQ ID NO 61
<211> LENGTH: 14
<212> TYPE: PRT
<213> ORGANISM: Homo sapiens

<400> SEQUENCE: 61

Phe Leu Ser Leu Gly Pro Phe Ser Asp Thr Thr Thr Val Lys
1               5                   10

<210> SEQ ID NO 62
<211> LENGTH: 22
<212> TYPE: PRT
<213> ORGANISM: Homo sapiens

<400> SEQUENCE: 62

Ile Ala Val Ile Gly His Ser Phe Gly Gly Ala Thr Val Ile Gln Thr
1               5                   10                  15

```
Leu Ser Glu Asp Gln Arg
        20

<210> SEQ ID NO 63
<211> LENGTH: 10
<212> TYPE: PRT
<213> ORGANISM: Homo sapiens

<400> SEQUENCE: 63

Val Gly Asp Thr Leu Asn Leu Asn Leu Arg
1               5                   10
```

EXTRACELLULAR AND MEMBRANE-ASSOCIATED PROSTATE CANCER MARKERS

CROSS REFERENCES TO RELATED APPLICATION

This application is a National Stage application under 35 U.S.C. §371 and claims benefit under 35 U.S.C. §119(a) of International Application No. PCT/US2007/079423, having an International Filing Date of Sep. 25, 2007, which claims the benefit of priority to U.S. Provisional Patent Application Ser. No. 60/847,057, filed on Sep. 25, 2006, the disclosures of which are incorporated herein by reference in their entirety.

BACKGROUND

1. Technical Field

This document relates to methods and materials involved in identifying, assessing, and monitoring prostate cancer in male mammals.

2. Background Information

Cancer is a general term for diseases characterized by uncontrolled, abnormal growth of cells. The resulting mass, or tumor, can invade and destroy surrounding normal tissues. In addition, cancer cells from the tumor can spread through the blood or lymph to start new cancers in other parts of the body, or metastases.

Prostate cancer occurs when a malignant tumor forms in the tissue of the prostate. The prostate is a gland in the male reproductive system located below the bladder and in front of the rectum. The main function of the prostate gland, which is about the size of a walnut, is to make fluid for semen. Although there are several cell types in the prostate, nearly all prostate cancers start in the gland cells. This type of cancer is known as adenocarcinoma.

Prostate cancer is the second leading cause of cancer-related death in American men. Most of the time, prostate cancer grows slowly. Autopsy studies show that many older men who died of other diseases also had prostate cancer that neither they nor their doctor were aware of. Sometimes, however, prostate cancer can grow and spread quickly. It is important to be able to distinguish prostate cancers that will grow slowly from those that will grow quickly since treatment can be especially effective when the cancer has not spread beyond the region of the prostate. Finding ways to detect cancers early can improve survival rates.

SUMMARY

This document provides methods and materials related to identifying, assessing, and monitoring prostate cancer in male mammals (e.g., humans). For example, this document provides arrays for detecting polypeptides or nucleic acids that can be used to identify prostate cancer in mammals. Such arrays can allow prostate cancer to be identified in mammals based on differences in the levels of many polypeptides or nucleic acids in biological samples from mammals that have prostate cancer as compared to the corresponding levels in biological samples from mammals that do not have prostate cancer.

Screening for prostate cancer has been widely performed by measuring serum levels of prostate-specific antigen (PSA). However, effective use of the PSA serum assay in general population screening is inhibited by a lack of sensitivity and specificity. Specific, sensitive, and non-invasive methods of screening mammals for cancer (e.g., prostate cancer) can allow cancer to be detected earlier. Early detection of cancer in mammals can allow the mammals to be treated sooner and improve their prognosis. Screening methods having adequate specificity with low false positive rates can reduce unnecessary treatment and suffering.

This document is based, in part, on the discovery of nucleic acid sequences that are predicted to encode extracellular or membrane-associated polypeptides, and that are differentially expressed in cancerous and non-cancerous prostate epithelial cells. This document also is based, in part, on the discovery of nucleic acid sequences that are predicted to encode polypeptides, and that are expressed in prostate cells at a high level relative to other cell types. The levels of transcripts and/or polypeptides encoded by these nucleic acids can be used to distinguish mammals with prostate cancer from mammals without prostate cancer. For example, a mammal that is found to have serum containing one or more than one polypeptide encoded by a nucleic acid listed in Table 2 at a level that is different (e.g., greater than or less than) than the average level observed in control serum can be classified as having prostate cancer. In some cases, a mammal that is found to have serum containing one or more than one polypeptide encoded by a nucleic acid listed in Table 2 and one or more than one polypeptide encoded by a nucleic acid listed in Table 3 at a level that is different (e.g., greater than or less than) than the average level observed in control serum can be classified as having prostate cancer. In some cases, a mammal that is found to have prostate cells expressing one or more than one polypeptide encoded by a nucleic acid listed in Table 4 at a level that is greater than the average level observed in control prostate cells can be classified as having prostate cancer. The levels of nucleic acids and/or polypeptides encoded by nucleic acids listed in Table 2 also can be used to evaluate cancer aggressiveness, monitor cancer progression, predict cancer outcome, and monitor response to treatment in mammals. In some cases, the level of one or more than one nucleic acid or polypeptide encoded by a nucleic acid listed in Table 2 and the level of one or more than one nucleic acid or polypeptide encoded by a nucleic acid listed in Table 3 can be used to evaluate cancer aggressiveness, monitor cancer progression, predict cancer outcome, or monitor the response to cancer treatment in mammals.

In general, one aspect of this document features a method for identifying a mammal as having prostate cancer. The method comprising, or consists essentially of, (a) determining whether or not a mammal has a prostate cancer fluid profile, and (b) classifying the mammal as having prostate cancer if the mammal has the prostate cancer fluid profile and classifying the mammal as not having prostate cancer if the mammal does not have the prostate cancer fluid profile. The mammal can be a human. The method can comprise using blood, serum, plasma, urine, semen, or seminal fluid to assess the presence or absence of the prostate cancer fluid profile.

In another aspect, this document features a method for identifying a mammal as having prostate cancer. The method comprises, or consists essentially of, (a) determining whether or not a mammal has a prostate cancer cell profile, and (b) classifying the mammal as having prostate cancer if the mammal has the prostate cancer cell profile and classifying the mammal as not having prostate cancer if the mammal does not have the prostate cancer cell profile. The mammal can be a human. The method can comprise using prostate cells obtained from a needle biopsy to assess the presence or absence of the prostate cancer cell profile.

In another aspect, this document features a method for assessing the effectiveness of a treatment for prostate cancer. The method comprises, of consists essentially of, determining whether or not a mammal having prostate cancer and having received a treatment for the prostate cancer has a prostate cancer fluid profile to the same or greater degree than that observed prior to the treatment, wherein the presence of the prostate cancer fluid profile to the same or greater degree than that observed prior to the treatment indicates that the treatment is ineffective. The mammal can be a human. The method can comprise using blood, serum, plasma, urine, semen, or seminal fluid to assess the presence or absence of the prostate cancer fluid profile to the same or greater degree than that observed prior to the treatment.

In another aspect, this document features a method for assessing the effectiveness of a treatment for prostate cancer. The method comprises, or consists essentially of, determining whether or not a mammal having prostate cancer and having received a treatment for the prostate cancer has a prostate cancer cell profile to the same or greater degree than that observed prior to the treatment, wherein the presence of the prostate cancer cell profile to the same or greater degree than that observed prior to the treatment indicates that the treatment is ineffective. The mammal can be a human. The method can comprise using prostate cells obtained from a needle biopsy to assess the presence or absence of the prostate cancer cell profile to the same or greater degree than that observed prior to the treatment.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references (e.g., the records associated with GenBank accession or GI numbers) mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to identifying, assessing, and monitoring prostate cancer in male mammals. For example, this document provides arrays for detecting nucleic acids or polypeptides that can be used to identify, assess, and/or monitor prostate cancer in male mammals. Such arrays can allow prostate cancer to be identified, assessed, and/or monitored based on the levels of nucleic acids or polypeptides in a biological sample from a mammal.

As described herein, this document provides methods and materials for identifying prostate cancer in male mammals (e.g., humans). In some embodiments, a mammal can be classified as having prostate cancer if it is determined that a biological fluid (e.g., blood, urine, seminal fluid, or serum) from the mammal contains one or more than one polypeptide (e.g., two, three, four, five, six, seven, eight, nine, 10, 15, 20, 25, 30, 35, 40, 45, 50, 55, 60, or more than 60 polypeptides), or a fragment thereof, encoded by a nucleic acid listed in Table 2 (e.g., a category 1, 2, or 3 nucleic acid listed in Table 2) at a level that is greater than the average level of the same one or more than one polypeptide observed in corresponding control fluid from control mammals. In some cases, a mammal can be classified as having prostate cancer if it is determined that a biological fluid (e.g., blood, urine, seminal fluid, or serum) from the mammal contains one or more than one polypeptide, or fragment thereof, encoded by a nucleic acid listed in Table 2, and one or more than one polypeptide, or fragment thereof, encoded by a nucleic acid listed in Table 3 at a level that is greater than the average level of the same one or more than one polypeptide observed in corresponding control fluid from control mammals. In some cases, a mammal can be classified as having prostate cancer if it is determined that prostate cells from the mammal contain one or more than one nucleic acid or polypeptide, or fragment thereof, encoded by a nucleic acid listed in Table 4 (e.g., a category 1, 2, or 3 nucleic acid listed in Table 4) at a level that is greater than the average level (e.g., via a subset analysis) of the same one or more than one nucleic acid or polypeptide in corresponding control (e.g., non-cancerous) prostate cells.

In some cases, a mammal can be classified as having prostate cancer if it is determined that a biological fluid (e.g., blood, urine, seminal fluid, or semen) from the mammal has a prostate cancer fluid profile. For the purpose of this document, the term "prostate cancer fluid profile" as used herein refers to a polypeptide profile in a biological fluid (e.g., blood, plasma, serum, urine, semen, or seminal fluid) where 16 or more (e.g., 18, 20, 25, 30, 35, 40, 45, 50, 55, 60, or more) polypeptides, or fragments thereof, encoded by nucleic acids listed in Table 2 are present at a level greater than the level observed in a corresponding control biological fluid from a control mammal. In some cases, the prostate cancer fluid profile can be a polypeptide profile in a biological fluid where 25, 30, 35, 40, 45, 50, 55, 60, 65, 70, 75, 80, 85, 90, 95, or 100 percent of the polypeptides, or fragments thereof, encoded by nucleic acids listed in Table 2 are present at a level greater than the level observed in corresponding control biological fluid from a control mammal.

In some cases, a mammal can be classified as having prostate cancer if it is determined that prostate cells from the mammal have a prostate cancer cell profile. The term "prostate cancer cell profile" as used herein refers to a profile where prostate cells express 12 or more (e.g., 15, 20, 25, 30, 35, 40, 45, 50, 55, 60, or more) nucleic acids or polypeptides, or fragments thereof, encoded by nucleic acids listed in Table 4 at a level greater than the level observed in corresponding control prostate cells. In some cases, the prostate cancer cell profile can be a profile in prostate cells where 25, 30, 35, 40, 45, 50, 55, 60, 65, 70, 75, 80, 85, 90, 95, or 100 percent of the nucleic acids or polypeptides, or fragments thereof, encoded by nucleic acids listed in Table 4 are present at a level greater than the level observed in corresponding control prostate cells.

Prostate cancer can be identified in any male mammal such as a male human, dog, horse, mouse, or rat. The mammal can be middle-aged or older. For example, a male human can be 35 years old or older (e.g., 40, 45, 50, 55, 60, 65, 70, 75 years old or older).

Any biological fluid can be evaluated to determine if it contains one or more than one polypeptide or nucleic acid, or fragment thereof, encoded by a nucleic acid listed in Table 2 at a level that is greater than the average level observed in a corresponding control biological fluid. For example, blood (e.g., peripheral blood or venous prostate blood), plasma, serum, urine, semen, and/or seminal fluid can be evaluated to determine if the fluid contains one or more than one polypeptide or nucleic acid encoded by a nucleic acid listed in Table 2 at a level that is greater than the average level observed in a corresponding control biological fluid. In some cases, a biological fluid (e.g., blood, plasma, serum, urine, semen, and/or seminal fluid) can be evaluated to determine if the fluid contains one or more than one polypeptide or nucleic acid, or fragment thereof, encoded by a nucleic acid listed in Table 2, and one or more than one polypeptide or nucleic acid, or fragment thereof, encoded by a nucleic acid listed in Table 3 at a level that is greater than the average level observed in a corresponding control biological fluid. In some cases, a biological fluid can be evaluated to determine if the fluid has a prostate cancer fluid profile.

Any type of biological sample can be evaluated to determine if it contains one or more than one nucleic acid or polypeptide, or fragment thereof, encoded by a nucleic acid listed in Table 4 at a level that is greater than the average level observed in a corresponding control biological sample. For example, biological fluids can be evaluated including, without limitation, blood, plasma, serum, urine, semen, and seminal fluid. In some cases, prostate cells can be evaluated including, without limitation, prostate cells in prostate tissue and metastatic prostate cancer cells in blood, urine, cellular fragments, or in tissues other than prostate tissue such as lung tissue and lymph node tissue. In some cases, prostate cells can be evaluated to determine whether or not the cells have a prostate cancer cell profile.

Any method can be used to obtain a biological sample from a mammal. For example, a blood sample can be obtained by peripheral venipuncture, and urine samples can be obtained using standard urine collection techniques. In some cases, a tissue sample can be obtained from a tissue biopsy (e.g., a needle biopsy), from a transurethral resection of the prostate (TURP), or from a radical prostatectomy. A sample can be manipulated prior to being evaluated for the level of one or more than one nucleic acid or polypeptide encoded by a nucleic acid listed in Table 2 or 3. A sample also can be manipulated prior to being evaluated for a prostate cancer fluid profile or a prostate cancer cell profile. For example, a prostate biopsy specimen can be frozen, embedded, and/or sectioned prior to being evaluated. In addition, nucleic acids and/or polypeptides can be extracted from a sample, purified, and evaluated to determine the level of one or more than one nucleic acid or polypeptide encoded by a nucleic acid listed in Table 2 or 3. In some cases, nucleic acids and/or polypeptides extracted from a sample can be evaluated for a prostate cancer cell profile or a prostate cancer fluid profile. In some cases, a tissue sample can be disrupted to obtain a cell lysate. Once obtained, the cell lysate can be analyzed for the level of one or more than one polypeptide encoded by a nucleic acid listed in Table 4. A cell lysate also can be evaluated for a prostate cancer cell profile. In some cases, prostate cells can be isolated from other cells or tissues prior to analysis. For example, prostate cells can be isolated from tissues using laser capture microdissection prior to being evaluated for the level of one or more than one nucleic acid or polypeptide encoded by a nucleic acid listed in Table 4. In some cases, prostate cells can be evaluated for a prostate cancer cell profile.

The level of any number of nucleic acids or polypeptides encoded by nucleic acids listed in Table 2 can be evaluated to identify prostate cancer. For example, the level of one or more than one (e.g., two, three, four, five, six, seven, eight, nine, 10, 15, 20, 25, 30, 35, 40, 45, 50, 55, 60, or more than 60) nucleic acid or polypeptide encoded by a nucleic acid listed in Table 2 can be used to identify prostate cancer. In some cases, the level of one or more than one (e.g., two, three, four, five, six, seven, eight, nine, 10, 15, 20, 25, 30, 35, 40, 45, 50, 55, 60, or more than 60) nucleic acid or polypeptide encoded by a nucleic acid listed in Table 2, and the level of one or more than one (e.g., two, three, four, five, six, or more than 6) nucleic acid or polypeptide encoded by a nucleic acid listed in Table 3 can be used to identify prostate cancer. In some cases, the level of one or more than one (e.g., two, three, four, five, six, seven, eight, nine, 10, 15, 20, 25, 30, 35, 40, 45, 50, or more than 50) nucleic acid or polypeptide encoded by a nucleic acid listed in Table 4 can be used to identify prostate cancer.

The level of a nucleic acid or polypeptide encoded by a nucleic acid listed in Table 2 or 3 in a biological sample can be greater than or less than the average level observed in corresponding control samples. Typically, a nucleic acid or polypeptide can be classified as being present at a level that is greater than or less than the average level observed in control samples if the levels differ by at least 10, 20, 30, 40, 50, 60, 70, 80, 90, or more percent. In some cases, a nucleic acid or polypeptide can be classified as being present at a level that is greater than or less than the average level observed in control samples if the levels differ by greater than 1-fold (e.g., 1.5-fold, 2-fold, 3-fold, or more than 3-fold). Control samples typically are obtained from one or more mammals of the same species as the mammal being evaluated. When identifying prostate cancer, control samples (e.g., control serum or urine samples) can be obtained from healthy mammals, such as male humans who do not have prostate cancer. In some cases, control samples can be non-cancerous prostate cells or tissues from male mammals having prostate cancer (e.g., non-neoplastic cells adjacent to prostate cancer cells). Control samples can be obtained from any number of mammals. For example, control samples can be obtained from one or more mammals (e.g., 10, 20, 30, 40, 50, 75, 100, 200, 300, 400, 500, 1000, or more than 1000 mammals) from the same species as the mammal being evaluated.

Any method can be used to determine whether or not a polypeptide is present in a biological sample at a level that is greater than or less than the average level observed in corresponding control samples. For example, the level of a particular polypeptide can be measured using, without limitation, immuno-based assays (e.g., ELISA and immunohistochemistry), Western blotting, arrays for detecting polypeptides, two-dimensional gel analysis, chromatographic separation, mass spectrometry (MS), tandem mass spectrometry (MS/MS), or liquid chromatography (LC)-MS. Methods of using arrays for detecting polypeptides include, without limitation, those described herein. Such methods can be used to determine simultaneously the relative levels of multiple polypeptides.

Any method can be used to determine whether or not a specific nucleic acid is present in a biological samples at a level that is greater than or less than the average level observed in corresponding control samples. For example, the level of a particular nucleic acid can be measured using, without limitation, Northern blotting, slot blotting, quantitative PCR, RT-PCR, or chip hybridization techniques. Methods for chip hybridization assays include, without limitation, those described herein. Such methods can be used to determine simultaneously the relative expression levels of multiple nucleic acids.

Methods provided herein for identifying prostate cancer in male mammals can be used in combination with one or more methods typically used to identify prostate cancer. Such methods include, without limitation, digital rectal exam, transrectal ultrasonography, intravenous pyelogram, cystoscopy, and blood and urine tests for levels of prostatic acid phosphatase (PAP) and PSA. A mammal can be evaluated regularly for prostate cancer. For example, a mammal can be evaluated once a year for as long as the mammal is alive. In some cases, male humans can be evaluated for prostate cancer once every year beginning at age 35. Mammals that are susceptible to develop prostate cancer can be screened more frequently, and screening can be started at an earlier age. For example, mammals having a genetic predisposition to develop cancer, a family history of cancer, or a trend towards an increased serum level of one or more polypeptides encoded by a nucleic acid listed in Table 2 can be assessed more frequently.

This document also provides materials and methods for assessing prostate cancer in a mammal. For example, this document provides materials and methods for assessing the aggressiveness of prostate cancer in a mammal. Methods typically used to assess the aggressiveness of prostate cancer in a mammal include determining the Gleason score, the serum PSA level, and whether or not the serum PSA level increases over time and rate of PSA increases (PSA velocity). The Gleason score is a measure of how different cancer cells are from normal cells. The more different the cancer cells are from non-cancer cells, the more likely that the cancer will spread quickly. In some cases, the aggressiveness of prostate cancer can be assessed based on the numbers and/or levels of nucleic acids or polypeptides encoded by nucleic acids listed in Table 2 in a biological fluid from a mammal. The greater the number of different nucleic acids or polypeptides encoded by nucleic acids listed in Table 2 in a biological fluid from the mammal, the more aggressive the prostate cancer in the mammal. In addition, the greater the differences between the levels of the nucleic acids or polypeptides encoded by nucleic acids listed in Table 2 in a biological fluid from a mammal and the average levels of the same nucleic acids or polypeptides in control samples, the more likely the prostate cancer will move rapidly and progress in the mammal. In some embodiments, the aggressiveness of prostate cancer can be assessed based on the levels of nucleic acids or polypeptides encoded by nucleic acids listed in Table 2, and the level of one or more than one nucleic acid or polypeptide encoded by a nucleic acid listed in Table 3 in a biological fluid from a mammal. In some cases, the levels of nucleic acids or polypeptides encoded by nucleic acids listed in Table 2 in a biological fluid can be used in combination with one or more other factors to determine whether or not a mammal having prostate cancer is susceptible to a poor outcome. For example, levels of nucleic acids or polypeptides encoded by nucleic acids listed in Table 2 in a biological fluid from a mammal having prostate cancer can be used in combination with the clinical stage, the serum PSA level, and/or the Gleason pattern of the prostate cancer to determine whether or not the mammal is likely to have to a poor outcome. In some cases, the aggressiveness of prostate cancer can be assessed based on the numbers and/or levels of nucleic acids or polypeptides encoded by nucleic acids listed in Table 4 in a biological sample from a mammal.

Information about the aggressiveness of prostate cancer can be used to guide treatment selection. For example, a mammal identified as having more aggressive prostate cancer can be treated earlier and more aggressively than a mammal identified as having less aggressive prostate cancer. A more aggressive treatment can include radical prostatectomy. A mammal identified as having less aggressive prostate cancer may undergo "watchful waiting" while having little or no standard treatment, particularly if the mammal is elderly.

Once prostate cancer has been identified in a mammal (e.g., a human), the mammal can be subsequently evaluated or monitored over time for progression of the cancer, particularly if the cancer was identified as being aggressive. For example, prostate cancer in a mammal can be assessed as having progressed if it is determined that a biological fluid from the mammal (e.g., serum or urine from the mammal) contains one or more than one nucleic acid or polypeptide encoded by a nucleic acid listed in Table 2 at a level that is greater than the level of the same one or more than one nucleic acid or polypeptide observed in a corresponding biological fluid (e.g., serum or urine) obtained previously from the same mammal. In some cases, prostate cancer in a mammal can be assessed as having progressed if it is determined that a biological fluid from the mammal (e.g., serum or urine from the mammal) contains one or more than one nucleic acid or polypeptide encoded by a nucleic acid listed in Table 2, and one or more than one nucleic acid or polypeptide encoded by a nucleic acid listed in Table 3 at a level that is greater than the level of the same one or more nucleic acids or polypeptides observed in a corresponding biological fluid (e.g., serum or urine) obtained previously from the same mammal. In some cases, prostate cancer in a mammal can be assessed as having progressed if it is determined that a biological fluid from the mammal has a prostate cancer fluid profile to a level greater than that observed in a corresponding biological fluid obtained previously from the same mammal. In some cases, prostate cancer in a mammal can be assessed as having progressed if it is determined that a sample (e.g., a sample of prostate cells) from the mammal contains one or more than one nucleic acid or polypeptide encoded by a nucleic acid listed in Table 4 at a level that is greater than the level of the same one or more than nucleic acid or polypeptide observed in a corresponding sample obtained previously from the same mammal. In some cases, prostate cancer in a mammal can be assessed as having progressed if it is determined that a sample (e.g., a sample of prostate cells) from the mammal has a prostate cancer cell profile to a level greater than that observed in a corresponding sample obtained previously from the same mammal. A mammal can be monitored for progression of prostate cancer over any period of time with any frequency. For example, a male mammal can be monitored once a year, twice a year, three times a year, or more frequently. In some cases, a mammal can be monitored every three months for five years or once a year for as long as the mammal is alive.

A mammal can also be assessed for progression of prostate cancer before, during, and after treatment for prostate cancer. For example, a mammal can be assessed for progression (e.g., metastasis) of prostate cancer while being treated with androgen deprivation therapy or following radical prostatectomy. Assessing a mammal for progression of prostate cancer during treatment of the mammal for prostate cancer can allow the effectiveness of the prostate cancer therapy to be determined. For example, a decrease in the level of one or more than one nucleic acid or polypeptide encoded by a nucleic acid listed in Table 2 in a biological fluid (e.g., serum or urine) from a mammal being treated for prostate cancer as compared to the level of the same one or more nucleic acids or polypeptides observed in a corresponding biological fluid (e.g., serum or urine) obtained previously from the same mammal can indicate that the therapy is effective. In some cases, a therapy can be assessed as being effective if it is determined that a fluid from a mammal having prostate cancer and having received a prostate cancer treatment has a prostate cancer fluid profile to a level less than that observed in corresponding fluid from the same mammal prior to the treatment.

This document also provides methods and materials to assist medical or research professionals in determining whether or not a mammal has prostate cancer. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of one or more than one polypeptide or nucleic acid encoded by a nucleic acid listed in Table 2 in a sample, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides arrays for detecting polypeptides. The arrays provided herein can be two-dimensional arrays, and can contain at least two different polypeptides capable of detecting polypeptides, such as antibodies (e.g., at least three, at least five, at least ten, at least 20, at least 30, at least 40, at least 50, or at least 60 different polypeptides capable of detecting polypeptides). The arrays provided herein also can contain multiple copies of each of many different polypeptides. In addition, the arrays for detecting polypeptides provided herein can contain polypeptides attached to any suitable surface (e.g., plastic or glass).

A polypeptide capable of detecting a polypeptide can be naturally occurring, recombinant, or synthetic. The polypeptides immobilized on an array also can be antibodies. An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a mouse, chicken, human, rabbit, sheep, or goat antibody. Such an antibody can be capable of binding specifically to a polypeptide encoded by a nucleic acid listed in Table 2 or 3. The polypeptides immobilized on the array can be members of a family such as a receptor family, protease family, or an enzyme family.

Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a nucleic acid encoding the partial antibody sequence. In some cases, an antibody fragment can be enzymatically or chemically produced by fragmentation of an intact antibody. In addition, numerous antibodies are available commercially (Table 1). An antibody directed against a polypeptide encoded by a nucleic acid listed in Table 2 or 3 can bind the polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

TABLE 1

Commercially available antibodies directed against extracellular or membrane-associated polypeptides

| Nucleic Acid Symbol | Antibody Name | Supplier | Catalog No. | Clone |
|---|---|---|---|---|
| APOC1 | Apolipoprotein C-1 antibody | Abcam, Cambridge, MA | ab20120 | mouse |
| ASPN | Asporin antibody | Imgenex, San Diego, CA | IMG-3803 | goat |
| C20orf102 | C20orf102 antibody | Abnova, Taipei, Taiwan | H00128434-M01 | clone 3B9 |
| COL2A1 | COL2A1 monoclonal antibody | Abnova, Taipei, Taiwan | H00001280-M01 | #3H1-9 |
| HLA-DMB | HLA-DMB monoclonal antibody | Abnova, Taipei, Taiwan | H00003109-M01 | clone 6B3 |
| MMP26 | Rabbit antibody to MMP-26 | Triple Point Biologics, Forest Grove, OR | RP3MMP26 | rabbit |
| NRN1 | Anti-human Neuritin antibody | R&D Systems, Minneapolis, MN | AF283 | goat |
| SFRP4 | SFRP4 polyclonal antibody | Abnova, Taipei, Taiwan | H00006424-A01 | mouse poly |
| CHRM3 | CHRM3 polyclonal antibody | Abnova, Taipei, Taiwan | H00001131-A01 | mouse poly |
| OR51E2 | PSGR antibody | Novus, Littleton, CO | ab13383 | rabbit |
| TMPRSS2 | TMPRSS2 (h-50) antibody | Santa Cruz Biotechnology, Santa Cruz, CA | sc-33533 | rabbit |
| PLA2G7 | PLA2G7 monoclonal antibody | Abnova, Taipei, Taiwan | H00007941-M02 | clone 5D1 |
| FZD8 | FZD8 polycolonal antibody | Abnova, Taipei, Taiwan | H00008325-A01 | mouse poly |

TABLE 1-continued

Commercially available antibodies directed against extracellular or membrane-associated polypeptides

| Nucleic Acid Symbol | Antibody Name | Supplier | Catalog No. | Clone |
|---|---|---|---|---|
| GJB1 | Connexin 32/GJB1 antibody [CXN-32] | Abcam, Cambridge, MA | ab11366 | CXN-32 |
| MSMB | Prostate Secretory Protein/PSP antibody [YPSP-1] | Abcam, Cambridge, MA | ab19070 | YPSP-1 |
| MSMB | MSMB polyclonal antibody | Abnova, Taipei, Taiwan | H00004477-A01 | mouse poly |
| MSMB | Mab to human Prostate Secretory protein | BIODESIGN, Saco, ME | M14841M | BDI841 |
| MSMB | Mab to human Prostate Secretory protein | BIODESIGN, Saco, ME | M14248M | BDI248 |
| MSMB | MSMB polyclonal antibody | Novus, Littleton, CO | H00004477-A01 | mouse poly |
| ADAMTS8 | ADAMTS8 antibody | Abcam, Cambridge, MA | ab28597 | rabbit |
| ADAMTS8 | ADAMTS8 monoclonal antibody | Abnova, Taipei, Taiwan | H00011095-M01 | clone 5A3 |
| ADAMTS8 | Rabbit anti ADAM-TS8, amino terminal | Accurate, Westbury, NY | ACL2ADAMTS8 | rabbit |
| ADAMTS8 | Rabbit anti ADAM-TS8, carboxy terminal | Accurate, Westbury, NY | ACL1ADAMTS8 | rabbit |
| ALDH3B2 | ALDH3B2 monoclonal antibody | Abnova, Taipei, Taiwan | H00000222-M01 | clone 3E6 |
| EFNA4 | Ephrin A4 Antibody | Novus, Littleton, CO | ab7041 | goat |
| GRIN3A | NMDAR3A + 3B | Abcam, Cambridge, MA | ab2639 | mouse |
| GRIN3A | NMDAR3A + 3B antibody | Novus, Littleton, CO | H00002904-A01 | mouse |
| GRIN3A | NMDAR NR3A/B antibody | QED, San Diego, CA | 60100 | rabbit |
| HPN | Hepsin antibody | Abcam, Cambridge, MA | ab31149 | Duck/IgY |
| HPN | Hepsin antibody | Abcam, Cambridge, MA | ab31148 | rabbit |
| HPN | HPN monoclonal antibody | Abnova, Taipei, Taiwan | H00003249-M01 | clone 3E3 |
| ITGBL1 | Osteoblast Specific Cysteine-rich Protein | Abcam, Cambridge, MA | ab37176 | chicken/IgY |
| LOX | LOX antibody | Abcam, Cambridge, MA | ab31238 | rabbit |
| MUC1 | MUC-1 polyclonal antibody | Abnova, Taipei, Taiwan | H00004582-A01 | mouse poly |
| NRP1 | NRP1 monoclonal antibody | Abnova, Taipei, Taiwan | H00008829-M05 | 1B3 |
| NRP1 | Anti-Neuropilin-1 (CUB Domain) | ECM Biosciences | NP2111 | rabbit |
| NRP1 | Neuropilin (A-12) antibody | Santa Cruz Biotechnology, Santa Cruz, CA | sc-5307 | mouse mono |
| PCDHB10 | PCDHB10 polyclonal antibody | Abnova, Taipei, Taiwan | H00056126-A01 | mouse poly |
| PCSK6 | PCSK6 plyclonal antibody | Abnova, Taipei, Taiwan | H00005046-A01 | mouse poly |
| PSCA | PSCA monoclonal antibody | Abnova, Taipei, Taiwan | H00008000-M03 | 5c2 |

Any method can be used to make an array for detecting polypeptides. For example, methods disclosed in U.S. Pat. No. 6,630,358 can be used to make arrays for detecting polypeptides. Arrays for detecting polypeptides can also be obtained commercially, such as from Panomics, Redwood City, Calif.

This document also provides nucleic acid arrays. The arrays provided herein can be two-dimensional arrays, and can contain at least two different nucleic acid molecules (e.g., at least three, at least five, at least ten, at least 20, at least 30, at least 40, at least 50, or at least 60 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or 25 and 50 nucleotides) in length. In some cases, an array can contain one or more cDNA molecules encoding, for example, partial or entire polypeptides. In addition, each nucleic acid molecule can have any sequence. For example, the nucleic acid molecules of the arrays provided herein can contain sequences that are present within the nucleic acids listed in Tables 2 and 3.

Typically, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within a nucleic acid listed in Table 2 or 3. For example, an array can contain 60 nucleic acid molecules located in known positions, where each of the 60 nucleic acid molecules is 100 nucleotides in length while containing a sequence that is (1) 30 nucleotides is length, and (2) 100 percent identical, over that 30 nucleotide length, to a sequence of one of the nucleic acids listed in Table 2. Thus, a nucleic acid molecule of an array provided herein can contain a sequence present within a nucleic acid listed in Table 2 or 3 where that sequence contains one or more (e.g., one, two, three, four, or more) mismatches.

The nucleic acid arrays provided herein can contain nucleic acid molecules attached to any suitable surface (e.g., plastic or glass). In addition, any method can be use to make a nucleic acid array. For example, spotting techniques and in situ synthesis techniques can be used to make nucleic acid arrays. Further, the methods disclosed in U.S. Pat. Nos. 5,744,305 and 5,143,854 can be used to make nucleic acid arrays.

In some cases, a sample from a mammal can be assessed for auto-antibodies against a polypeptide encoded by any of the nucleic acid molecules provided herein. The presence of such auto-antibodies can indicate that the mammal has prostate cancer. For example, a blood sample from a human can be assessed for the presence of auto-antibodies to a polypeptide encoded by any of the nucleic acid molecules provided herein with the presence of such an auto-antibody indicating that that human has prostate cancer.

The invention will be further described in the following examples, which do not limit the scope of the invention described in the claims.

EXAMPLES

Example 1

Identification of Nucleic Acids Encoding Extracellular and Membrane-Associated Polypeptides that can be used to Identify Prostate Cancer Gene expression was profiled in prostate epithelial cells. Benign and malignant cells were laser capture microdissected from 100 prostate tissues and metastatic prostatic adenocarcinomas. Non-neoplastic prostate epithelial cells were collected from the tissues of 29 patients having prostate cancer. High-grade prostatic intraepithelial neoplasia (PIN) cells, metastatic prostate cancer cells, and primary Gleason pattern 3, 4, and 5 cells were collected from the remaining tissues. RNA was extracted from homogenous populations of captured cells and purified. Samples of total RNA were linearly amplified, labeled, and hybridized to U133 Plus 2.0 arrays (Affymetrix, Santa Clara, Calif.). The arrays were washed, stained, and scanned in accordance with Affymetrix protocols.

Secreted and membrane bound polypeptides associated with the Affymetrix probe sets were identified using two methods. First, RefSeq polypeptide sequence identifiers annotated to the probe set identifiers were abstracted from the Affymetrix U133 Plus 2.0 annotation file. These sequences were downloaded from NCBI and processed through a prediction pipeline, which included SignalP analysis, TargetP analysis, TMHMM analysis, and Phobius analysis. Polypeptides predicted to be secretory polypeptides by the SignalP and TargetP programs were further analyzed using the TMHMM and Phobius programs. Polypeptides that were not predicted to be secretory polypeptides by the SignalP program or the TargetP program were classified as non-secretory polypeptides. Secretory polypeptides predicted to have no transmembrane domains by the TMHMM program were classified as extracellular. Secretory polypeptides predicted to have two or more transmembrane domains were classified as membrane-associated polypeptides. Secretory polypeptides predicted to have only one transmembrane domain were analyzed using the Phobius program. Phobius predictions were used to differentiate polypeptides with N-terminal signal anchors (uncleaved) from polypeptides with N-terminal signal sequences (cleaved). The second method used to identify secreted and membrane polypeptides involved mining the localization annotated database of SWISS-PROT polypeptides. The SwissProt records for all human polypeptides were downloaded. All localization annotations were manually reviewed and categorized as extracellular (S), plasma membrane (M), or intracellular (I). All probe sets with annotated SwissProt polypeptides having cellular localization annotations were classified extracellular (S), plasma membrane (M), or intracellular (I). Localization classifications assigned by SwissProt annotations were given preference over classifications made by the prediction analyses. A set of 70 nucleic acids encoding extracellular and membrane-associated polypeptides was identified, including 53 nucleic acids that were annotated or predicted to encode extracellular polypeptides, and 17 nucleic acids that were annotated or predicted to encode membrane-associated polypeptides.

The value of the selected nucleic acids for use in identifying cancer was assessed using two methods. Fifty-four polypeptides, including all of the membrane-associated polypeptides, were selected based on up-regulation of corresponding RNA transcripts observed in prostate cancer cells as compared to non-neoplastic prostate cells. The initial list of differentially expressed nucleic acids was identified using several microarray analysis parameters, including:
 a. PM/MM normalization and no transformation
 b. PM only normalization and no transformation
 c. PM/MM normalization and log2 transformation
 d. PM only normalization and log2 transformation Expression values generated from these analysis methods were then used to make the following comparisons:
 a. Gleason pattern 3 versus
   Non-neoplastic (excluding Benign Prostatic Hyperplasia (BPH))
 b. Gleason pattern 3 versus
   Non-neoplastic+BPH
 c. Gleason pattern 3+Gleason pattern 4 versus
   Non-neoplastic (excluding BPH)
 d. Gleason pattern 3+Gleason pattern 4 versus
   Non-neoplastic+BPH
 e. All Cancer versus
   Non-neoplastic (excluding BPH)
 f. All Cancer versus
   Non-neoplastic+BPH Nucleic acids demonstrating at least two fold up-regulation in cancer cells compared to non-neoplastic cells were cross-referenced with nucleic acids classified as encoding either secretory or membrane-associated polypeptides. The resulting list of nucleic acids was manually curated to remove cases with expression levels below the noise level of the microarray experiment, and cases having an expression profile that was over-biased by one or two aberrant cases.

The remaining sixteen nucleic acids were selected because they had a high level of expression in prostate cells and a prostate-preferential expression profile, without clear differential expression between cancer and non-cancer cells. Tissue specificity was quantitated by mining Expressed Sequence Tag transcripts.

The 70 nucleic acids selected were cross-referenced with the Cancer Genome Anatomy Project's SAGE Genie, the Ludwig Institute for Cancer Research MPSS database, the Human Protein Atlas database, and an EST tissue specificity analysis database. Based on these additional transcriptomic and immunohistochemistry annotations, the nucleic acids were prioritized with numeric rankings from 1 (highest priority) to three (lowest priority). The selected nucleic acids are listed in Tables 2-4.

TABLE 2

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| APOC1 | Increased expression in cancer cells versus non-cancer cells | NP_001636.1 | 1 | Extracellular |
| ASPN | Increased expression in cancer cells versus non-cancer cells | NP_060150.3 | 1 | Extracellular |
| BCMP11 | Increased expression in cancer cells versus non-cancer cells | NP_789783.1 | 1 | Extracellular |
| C20orf102 | Increased expression in cancer cells versus non-cancer cells | NP_542174.1 | 1 | Extracellular |
| COL2A1 | Increased expression in cancer cells versus non-cancer cells | NP_001835.2 NP_149162.1 | 1 | Extracellular |
| F5 | Increased expression in cancer cells versus non-cancer cells | NP_000121.1 | 1 | Extracellular |
| HLA-DMB | Increased expression in cancer cells versus non-cancer cells | NP_002109.1 | 1 | Extracellular |
| LRRN1 | Increased expression in cancer cells versus non-cancer cells | NP_065924.2 | 1 | Extracellular |
| MMP26 | Increased expression in cancer cells versus non-cancer cells | NP_068573.2 | 1 | Extracellular |
| NRN1 | Increased expression in cancer cells versus non-cancer cells | NP_057672.1 | 1 | Extracellular |
| OGDHL | Increased expression in cancer cells versus non-cancer cells | NP_060715.1 | 1 | Extracellular |
| PLA1A | Increased expression in cancer cells versus non-cancer cells | NP_056984.1 | 1 | Extracellular |
| PLA2G7 | Increased expression in cancer cells versus non-cancer cells | NP_005075.2 | 1 | Extracellular |
| SFRP4 | Increased expression in cancer cells versus non-cancer cells | NP_003005.1 | 1 | Extracellular |
| ALDH3B2 | Increased expression in cancer cells versus non-cancer cells | NP_000686.2 NP_001026786.1 | 2 | Extracellular |

TABLE 2-continued

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| APOF | Increased expression in cancer cells versus non-cancer cells | NP_001629.1 | 2 | Extracellular |
| B3Gn-T6 | Increased expression in cancer cells versus non-cancer cells | NP_619651.2 | 2 | Extracellular |
| C4A /// C4B | Increased expression in cancer cells versus non-cancer cells | NP_001002029.1 NP_009224.2 | 2 | Extracellular |
| COL9A2 | Increased expression in cancer cells versus non-cancer cells | NP_001843.1 | 2 | Extracellular |
| COMP | Increased expression in cancer cells versus non-cancer cells | NP_000086.2 | 2 | Extracellular |
| CXCL11 | Increased expression in cancer cells versus non-cancer cells | NP_005400.1 | 2 | Extracellular |
| CXCL14 | Increased expression in cancer cells versus non-cancer cells | NP_004878.2 | 2 | Extracellular |
| CXCL9 | Increased expression in cancer cells versus non-cancer cells | NP_002407.1 | 2 | Extracellular |
| DHRS8 | Increased expression in cancer cells versus non-cancer cells | NP_057329.1 | 2 | Extracellular |
| ITGBL1 | Increased expression in cancer cells versus non-cancer cells | NP_004782.1 | 2 | Extracellular |
| LOX | Increased expression in cancer cells versus non-cancer cells | NP_002308.2 | 2 | Extracellular |
| MUC1 | Increased expression in cancer cells versus non-cancer cells | NP_001018016.1 NP_001018017.1 NP_001018021.1 NP_002447.4 | 2 | Extracellular |
| OR51E1 | Increased expression in cancer cells versus non-cancer cells | NP_689643.1 | 2 | Extracellular |
| PCSK6 | Increased expression in cancer cells versus non-cancer cells | NP_002561.1 NP_612192.1 NP_612193.1 NP_612194.1 NP_612195.1 NP_612196.1 NP_612197.1 NP_612198.2 | 2 | Extracellular |
| RPL22L1 | Increased expression in cancer cells versus non-cancer cells | XP_498952.2 XP_940025.1 XP_947405.1 XP_950994.1 | 2 | Extracellular |
| C1orf64 | Increased expression in cancer cells versus non-cancer cells | NP_849162.1 | 3 | Extracellular |
| CCL19 | Increased expression in cancer cells versus non-cancer cells | NP_006265.1 | 3 | Extracellular |
| NRP1 | Increased expression in cancer cells versus non-cancer cells | NP_001019799.1 NP_001019800.1 NP_003864.3 | 3 | Extracellular |
| SFTPA2 | Increased expression in cancer cells versus non-cancer cells | NP_008857.1 | 3 | Extracellular |
| CDH10 | Increased expression in cancer cells versus non-cancer cells | NP_006718.2 | 1 | Membrane-associated |
| CDH7 | Increased expression in cancer cells versus non-cancer cells | NP_004352.2 NP_387450.1 | 1 | Membrane-associated |
| CHRM3 | Increased expression in cancer cells versus non-cancer cells | NP_000731.1 | 1 | Membrane-associated |

TABLE 2-continued

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| FZD8 | Increased expression in cancer cells versus non-cancer cells | NP_114072.1 | 1 | Membrane-associated |
| GJB1 | Increased expression in cancer cells versus non-cancer cells | NP_000157.1 | 1 | Membrane-associated |
| MS4A8B | Increased expression in cancer cells versus non-cancer cells | NP_113645.1 | 1 | Membrane-associated |
| OR51E2 | Increased expression in cancer cells versus non-cancer cells | NP_110401.1 | 1 | Membrane-associated |
| SLC43A1 | Increased expression in cancer cells versus non-cancer cells | NP_003618.1 | 1 | Membrane-associated |
| TMEM45B | Increased expression in cancer cells versus non-cancer cells | NP_620143.1 | 1 | Membrane-associated |
| FAM77C | Increased expression in cancer cells versus non-cancer cells | NP_078798.1 | 2 | Membrane-associated |
| GPR116 | Increased expression in cancer cells versus non-cancer cells | NP_056049.3 | 2 | Membrane-associated |
| GRIN3A | Increased expression in cancer cells versus non-cancer cells | NP_597702.1 | 2 | Membrane-associated |
| HPN | Increased expression in cancer cells versus non-cancer cells | NP_002142.1 NP_892028.1 | 2 | Membrane-associated |
| PCDHB10 | Increased expression in cancer cells versus non-cancer cells | NP_061753.1 | 2 | Membrane-associated |
| PCDHGA4 | Increased expression in cancer cells versus non-cancer cells | NP_061740.1 NP_114442.1 | 2 | Membrane-associated |
| PRG-3 | Increased expression in cancer cells versus non-cancer cells | NP_060223.2 NP_997182.1 | 2 | Membrane-associated |
| RET | Increased expression in cancer cells versus non-cancer cells | NP_065681.1 NP_066124.1 | 2 | Membrane-associated |
| ACPP | High-level, prostate-preferential expression | NP_001090.2 | 1 | Extracellular |
| FAM61B | High-level, prostate-preferential expression | NP_653304.1 | 1 | Extracellular |
| MSMB | High-level, prostate-preferential expression | NP_002434.1 NP_619540.1 | 1 | Extracellular |
| PGLS | High-level, prostate-preferential expression | NP_036220.1 | 1 | Extracellular |
| RBM35A | High-level, prostate-preferential expression | NP_001030087.1 NP_060167.2 | 1 | Extracellular |
| TMPRSS2 | High-level, prostate-preferential expression | NP_005647.2 | 1 | Extracellular |
| LOC284591 | High-level, prostate-preferential expression | XP_932207.1 XP_941863.1 | 2 | Extracellular |
| ADAMTS8 | High-level, prostate-preferential expression | NP_008968.3 | 2 | Extracellular |
| EFNA4 | High-level, prostate-preferential expression | NP_005218.1 NP_872631.1 NP_872632.1 | 3 | Extracellular |
| KAZALD1 | High-level, prostate-preferential expression | NP_112191.2 | 3 | Extracellular |
| SEMA3F | High-level, prostate-preferential expression | NP_004177.2 | 3 | Extracellular |
| UCN | High-level, prostate-preferential expression | NP_003344.1 | 3 | Extracellular |
| PRAC2 | High-level, prostate-preferential expression | Entrez Gene 360205 | 3 | Extracellular |

TABLE 3

Nucleic acids encoding extracellular polypeptides that can be used in combination with one or more polypeptides encoded by nucleic acids listed in Table 2 to identify prostate cancer.

| Nucleic Acid Symbol | Selection Process | RefSeq Protein Identifier | Category | Localization |
|---|---|---|---|---|
| CRISP3 | Increased expression in cancer cells versus non-cancer cells | NP_006052.1 | 1 | Extracellular |
| AMACR | Increased expression in cancer cells versus non-cancer cells | NP_055139.4 NP_976316.1 | 3 | Extracellular |
| KLK2 | High-level, prostate-preferential expression | NP_001002231.1 NP_001002232.1 NP_005542.1 | 1 | Extracellular |
| KLK3 | High-level, prostate-preferential expression | NP_001025218.1 NP_001025219.1 NP_001025220.1 NP_001025221.1 NP_001639.1 | 1 | Extracellular |
| KLK4 | High-level, prostate-preferential expression | NP_004908.2 | 2 | Extracellular |
| PSCA | High-level, prostate-preferential expression | NP_005663.1 | 2 | Extracellular |

TABLE 4

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| APOC1 | Increased expression in cancer cells versus non-cancer cells | NP_001636.1 | 1 | Extracellular |
| ASPN | Increased expression in cancer cells versus non-cancer cells | NP_060150.3 | 1 | Extracellular |
| BCMP11 | Increased expression in cancer cells versus non-cancer cells | NP_789783.1 | 1 | Extracellular |
| C20orf102 | Increased expression in cancer cells versus non-cancer cells | NP_542174.1 | 1 | Extracellular |
| COL2A1 | Increased expression in cancer cells versus non-cancer cells | NP_001835.2 NP_149162.1 | 1 | Extracellular |
| F5 | Increased expression in cancer cells versus non-cancer cells | NP_000121.1 | 1 | Extracellular |
| HLA-DMB | Increased expression in cancer cells versus non-cancer cells | NP_002109.1 | 1 | Extracellular |
| LRRN1 | Increased expression in cancer cells versus non-cancer cells | NP_065924.2 | 1 | Extracellular |
| MMP26 | Increased expression in cancer cells versus non-cancer cells | NP_068573.2 | 1 | Extracellular |
| NRN1 | Increased expression in cancer cells versus non-cancer cells | NP_057672.1 | 1 | Extracellular |
| OGDHL | Increased expression in cancer cells versus non-cancer cells | NP_060715.1 | 1 | Extracellular |
| PLA1A | Increased expression in cancer cells versus non-cancer cells | NP_056984.1 | 1 | Extracellular |
| PLA2G7 | Increased expression in cancer cells versus non-cancer cells | NP_005075.2 | 1 | Extracellular |
| SFRP4 | Increased expression in cancer cells versus non-cancer cells | NP_003005.1 | 1 | Extracellular |

TABLE 4-continued

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| ALDH3B2 | Increased expression in cancer cells versus non-cancer cells | NP_000686.2<br>NP_001026786.1 | 2 | Extracellular |
| APOF | Increased expression in cancer cells versus non-cancer cells | NP_001629.1 | 2 | Extracellular |
| B3Gn-T6 | Increased expression in cancer cells versus non-cancer cells | NP_619651.2 | 2 | Extracellular |
| C4A /// C4B | Increased expression in cancer cells versus non-cancer cells | NP_001002029.1<br>NP_009224.2 | 2 | Extracellular |
| COL9A2 | Increased expression in cancer cells versus non-cancer cells | NP_001843.1 | 2 | Extracellular |
| COMP | Increased expression in cancer cells versus non-cancer cells | NP_000086.2 | 2 | Extracellular |
| CXCL11 | Increased expression in cancer cells versus non-cancer cells | NP_005400.1 | 2 | Extracellular |
| CXCL14 | Increased expression in cancer cells versus non-cancer cells | NP_004878.2 | 2 | Extracellular |
| CXCL9 | Increased expression in cancer cells versus non-cancer cells | NP_002407.1 | 2 | Extracellular |
| DHRS8 | Increased expression in cancer cells versus non-cancer cells | NP_057329.1 | 2 | Extracellular |
| ITGBL1 | Increased expression in cancer cells versus non-cancer cells | NP_004782.1 | 2 | Extracellular |
| LOX | Increased expression in cancer cells versus non-cancer cells | NP_002308.2 | 2 | Extracellular |
| MUC1 | Increased expression in cancer cells versus non-cancer cells | NP_001018016.1<br>NP_001018017.1<br>NP_001018021.1<br>NP_002447.4 | 2 | Extracellular |
| OR51E1 | Increased expression in cancer cells versus non-cancer cells | NP_689643.1 | 2 | Extracellular |
| PCSK6 | Increased expression in cancer cells versus non-cancer cells | NP_002561.1<br>NP_612192.1<br>NP_612193.1<br>NP_P612194.1<br>NP_P612195.1<br>NP_P612196.1<br>NP_612197.1<br>NP_612198.2 | 2 | Extracellular |
| RPL22L1 | Increased expression in cancer cells versus non-cancer cells | XP_498952.2<br>XP_940025.1<br>XP_947405.1<br>XP_950994.1 | 2 | Extracellular |
| C1orf64 | Increased expression in cancer cells versus non-cancer cells | NP_849162.1 | 3 | Extracellular |
| CCL19 | Increased expression in cancer cells versus non-cancer cells | NP_006265.1 | 3 | Extracellular |
| NRP1 | Increased expression in cancer cells versus non-cancer cells | NP_001019799.1<br>NP_001019800.1<br>NP_003864.3 | 3 | Extracellular |
| SFTPA2 | Increased expression in cancer cells versus non-cancer cells | NP_008857.1 | 3 | Extracellular |

TABLE 4-continued

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| CDH10 | Increased expression in cancer cells versus non-cancer cells | NP_006718.2 | 1 | Membrane-associated |
| CDH7 | Increased expression in cancer cells versus non-cancer cells | NP_004352.2 NP_387450.1 | 1 | Membrane-associated |
| CHRM3 | Increased expression in cancer cells versus non-cancer cells | NP_000731.1 | 1 | Membrane-associated |
| FZD8 | Increased expression in cancer cells versus non-cancer cells | NP_114072.1 | 1 | Membrane-associated |
| GJB1 | Increased expression in cancer cells versus non-cancer cells | NP_000157.1 | 1 | Membrane-associated |
| MS4A8B | Increased expression in cancer cells versus non-cancer cells | NP_113645.1 | 1 | Membrane-associated |
| OR51E2 | Increased expression in cancer cells versus non-cancer cells | NP_110401.1 | 1 | Membrane-associated |
| SLC43A1 | Increased expression in cancer cells versus non-cancer cells | NP_003618.1 | 1 | Membrane-associated |
| TMEM45B | Increased expression in cancer cells versus non-cancer cells | NP_620143.1 | 1 | Membrane-associated |
| FAM77C | Increased expression in cancer cells versus non-cancer cells | NP_078798.1 | 2 | Membrane-associated |
| GPR116 | Increased expression in cancer cells versus non-cancer cells | NP_056049.3 | 2 | Membrane-associated |
| GRIN3A | Increased expression in cancer cells versus non-cancer cells | NP_597702.1 | 2 | Membrane-associated |
| HPN | Increased expression in cancer cells versus non-cancer cells | NP_002142.1 NP_892028.1 | 2 | Membrane-associated |
| PCDHB10 | Increased expression in cancer cells versus non-cancer cells | NP_061753.1 | 2 | Membrane-associated |
| PCDHGA4 | Increased expression in cancer cells versus non-cancer cells | NP_061740.1 NP_114442.1 | 2 | Membrane-associated |
| PRG-3 | Increased expression in cancer cells versus non-cancer cells | NP_060223.2 NP_997182.1 | 2 | Membrane-associated |
| RET | Increased expression in cancer cells versus non-cancer cells | NP_065681.1 NP_066124.1 | 2 | Membrane-associated |

Example 2

Antibodies for Enriching Polypeptide Concentrations within a Serum Sample

Immunoaffinity reagents were developed to extract and concentrate particular polypeptide fragments (e.g., trypsin-digested polypeptide fragments) corresponding to identified biomarkers (Table 5). Bioinformatics techniques were used to predict those polypeptide sequences that possess the following characteristics:

(1) an amino acid sequence that is unique to the predicted biomarker (2) a sequence that is predicted to be immunogenic for the production of antisera.

(3) the ability for the polypeptide and its fragments to produce a good charge/mass signal on tandem MS/MS (4) a sequence that is unlikely to undergo post-translation modifications such as phosphorylation or glycosylation so the circulating forms can match a synthetic form of the polypeptide.

TABLE 5

List of biomarkers.

| Marker | Annotated Localization | Bioinformatics SignalP* | TargetP# | TM† | Partnership Microarray Up-Regulated | Differential (% 2x 2nd normal) | PMID16286247 Microarray Up-Regulated | differential (% 2x 2nd normal) |
|---|---|---|---|---|---|---|---|---|
| ALDH3B2 |  | N | S | 0 | ↑ | 50%-75% | ↑ | 50%-75% |
| APOC1 | Secreted polypeptide | Y | S | 0 | ↑ | 25%-50% | ↔ |  |
| APOF | Secreted polypeptide | Y | na | 0 | ↑ | 25%-50% | ↔ |  |
| ASPN | Secreted polypeptide; extracellular space; extracellular matrix | Y | S | 0 | ↑ | 25%-50% | ↑ | 25%-50% |
| B3GNT6 |  |  |  |  | ↑ | 25%-50% | ↔ |  |
| C1orf64 |  | N | — | 0 | ↑ | 0%-25% | ↔ |  |
| C4A /// C4B |  | Y | S | 0 | ↑ | 0%-25% | ↑ | 50%-75% |
| CCL19 | Secreted polypeptide | Y | S | 0 | ↑ | 0%-25% | ↔ |  |
| CDH10 | Membrane; single-pass type I membrane polypeptide (Potential) | Y | S | 1 | ↑ | 25%-50% | ↔ |  |
| CDH7 | Membrane; single-pass type I membrane polypeptide | Y | S | 1 | ↑ | 25%-50% | ↔ |  |
| COL2A1 |  | Y | S | 0 | ↑ | 25%-50% | ↑ | 50%-75% |
| COL9A2 |  | Y | S | 0 | ↑ | 25%-50% | ↑ | 50%-75% |
| COMP | Secreted polypeptide | Y | S | 0 | ↑ | 0%-25% | ↔ |  |
| CXCL11 | Secreted polypeptide | Y | S | 1 | ↑ | 0%-25% | ↔ |  |
| CXCL14 | Secreted polypeptide | Y | S | 1 | ↑ | 0%-25% | ↑ | 50%-75% |
| CXCL9 | Secreted polypeptide | Y | S | 1 | ↑ | 0%-25% | ↔ |  |
| EFNA4 |  | Y | na | 0 | ↔ |  | ↔ |  |
| F5 |  | Y | S | 0 | ↑ | 25%-50% | ↑ | 50%-75% |
| FAM77C | Membrane; multi-pass membrane polypeptide (Potential) | Y | S | 2 | ↑ | 25%-50% | ↔ |  |
| GPR116 | Membrane; multi-pass membrane polypeptide (Potential) | Y | S | 7 | ↑ | 0%-25% | ↔ |  |
| KAZALD1 | Secreted polypeptide (Probable) | Y | na | 0 | ↑ | 0%-25% | ↔ |  |
| LOC284591 |  | Y | na | 0 |  |  | ↔ |  |
| LOX | Secreted polypeptide; extracellular space | Y | S | 0 | ↑ | 25%-50% | ↔ |  |
| LRRN1 | Membrane; single-pass type I membrane | Y | S | 1 | ↑ | 25%-50% | ↓ |  |

TABLE 5-continued

List of biomarkers.

| Marker | Annotated Localization | Bioinformatics | | | Partnership Microarray Differential Up-Regulated | 2nd normal (% 2x) | PMID16286247 Microarray Up-Regulated | differential (% 2x 2nd normal) |
|---|---|---|---|---|---|---|---|---|
| | | SignalP* | TargetP# | TM† | | | | |
| LSM14 (FAM61B) | polypeptide (Potential) | Y | na | 0 | ↔ | | | |
| MS4A8B | Membrane; multi-pass membrane polypeptide | N | S | 4 | ↑ | 50%-75% | ↔ | |
| NRN1 | Cell membrane; lipid-anchor; GPI-anchor (Potential) | Y | S | 0 | ↑ | 25%-50% | ↔ | |
| OGDHL | | Y | M | 0 | ↑ | 25%-50% | ↔ | |
| PCDHB10 | Membrane; single-pass type I membrane polypeptide (By similarity) | Y | S | 2 | ↑ | 50%-75% | ↔ | |
| PCDHGA4 | Membrane; single-pass type I membrane polypeptide (By similarity) | Y | S | 1 | ↑ | 0%-25% | ↑ | 50%-75% |
| PCSK6 | | N | S | 0 | ↑ | 0%-25% | ↔ | |
| PGLS | | | | | ↔ | | ↔ | |
| RBM35A | | Y | na | 0 | ↔ | | ↔ | |
| RP11-35N6.1 (PRG-3) | | Y | S | 6 | ↑ | 25%-50% | | |
| RPL22L1 | | N | S | 0 | ↑ | 25%-50% | | |

*= D-score prediction of N-terminal signal peptide presence by SignalP 3.0;
= default prediction of N-terminal signal peptide presence by TargetP 1.1;
†= number of transmembrane domains predicted by TMHMM 2.0. The Partnership Microarray columns represent data from an internally generated prostate cancer microarray expression dataset. The PMID (PubMed ID) 16286247 columns describe the expression of the target genes in an externally created, public microarray prostate cancer dataset described elsewhere (Varambally et al., Cancer Cell., 8(5): 393-406 (2005)).

48 particular polypeptide fragments were identified (Table 6). Of these, 43 polypeptide fragments were synthesized and 39 were used to immunize rabbits as KLH conjugates. Briefly, the polypeptides were verified for the correct molecular mass by ESI mass spectrometry. Each polypeptide contained a cysteine residue added to either the N-terminal or C-terminal for conjugation of KLH.

TABLE 6

Polypeptide fragment sequences.

| Gene | Offset | Length | Sequence | SEQ ID NO: |
|---|---|---|---|---|
| APOF | 295 | 13 | SYDLDPGAGSLEI | 1 |
| CDH7 | 142 | 10 | IQDINDNEPK | 2 |
| COL9A2 | 408 | 18 | GEQGPPGIPGPQGLPGVK | 3 |
| COMP | 36 | 13 | ELQETNAALQDVR | 4 |
| COMP | 485 | 12 | LVPNPGQEDADR | 5 |
| LOX | 270 | 13 | NQGTSDFLPSRPR | 6 |
| LOX | 33 | 10 | EPPAAPGAWR | 7 |
| PCDHGA4 | 141 | 10 | VAENENPGAR | 8 |
| COL2A1 | 542 | 18 | GANGDPGRPGEPGLPGAR | 9 |
| COL2A1 | 940 | 16 | AGEPGLQGPAGPPGEK | 10 |
| COL2A1 | 119 | 15 | GPPGPQGPAGEQGPR | 11 |
| COL9A2 | 70 | 19 | AGPDGPDGKPGIDGLTGAK | 12 |

TABLE 6-continued

Polypeptide fragment sequences.

| Gene | Offset | Length | Sequence | SEQ ID NO: |
|---|---|---|---|---|
| COL9A2 | 198 | 15 | GILGDPGHQGKPGPK | 13 |
| PCDHGA4 | 265 | 17 | ATDPDEGANGDVTYSFR | 14 |
| ALDH3B2 | 121 | 12 | HLTPVTLELGGK | 15 |
| APOF | 232 | 14 | SGVQQLIQYYQDQK | 16 |
| ASPN | 153 | 17 | LYLSHNQLSEIPLNLPK | 17 |
| ASPN | 236 | 15 | GLPPTLLELHLDYNK | 18 |
| C4A | 756 | 19 | ALEILQEEDLIDEDDIPVR | 19 |
| C4A | 138 | 17 | GHLFLQTDQPIYNPGQR | 20 |
| C4A | 1352 | 13 | GLEEELQFSLGSK | 21 |
| F5 | 1580 | 19 | NYYIAAEEISWDYSEFVQR | 22 |
| F5 | 2151 | 14 | SYTIHYSEQGVEWK | 23 |
| KAZALD1 | 207 | 19 | DGLDIQLPGDDPHISVQFR | 24 |
| OGDHL | 673 | 11 | HHVLHDQEVDR | 25 |
| PCDHB10 | 72 | 17 | QYLLLDSHTGNLLTNEK | 26 |
| PCDHB10 | 124 | 12 | DINDHAPVFQDK | 27 |
| PGLS | 214 | 21 | ILEDQEENPLPAALVQPHTGK | 28 |
| RPL22L1 | 15 | 24 | FNLDLTHPVEDGIFDSGNFEQFLR | 29 |
| B3GNT1 | 162 | 9 | YEAAVPDPR | 30 |
| C1orf64 | 19 | 11 | ETGLETSSGGK | 31 |
| CDH10 | 688 | 11 | DIIPETLFIPR | 32 |
| CDH10 | 347 | 11 | VEAENTHVDPR | 33 |
| GRP119 | 859 | 10 | SSHPETYQQR | 34 |
| LRRN1 | 355 | 9 | TVESLPNLR | 35 |
| LRRN1 | 562 | 11 | IDNPHITYTAR | 36 |
| LSM14B | 178 | 10 | GTTGTQLNGR | 37 |
| PCSK6 | 136 | 8 | WLQQEVK | 38 |
| PCSK6 | 597 | 17 | AEGQWTLEIQDLPSQVR | 39 |
| RBM35A | 230 | 13 | GLPWQSSDQDIAR | 40 |
| NRN1 | 91 | 17 | DKLRKESKNLNIQGSKF | 41 |
| FAM77C | 144 | 11 | IEALSSALQIF | 42 |
| EFNA4 | 15 | 16 | LGSPLRGGSSLRHVVY | 43 |
| KLK3 | 125 | 12 | LSEPAELTDAVK | 44 |
| KLK3 | 33 | 12 | HSQPWQVLVASR | 45 |
| HK2 | 501 | 9 | ETHASAPVK | 46 |
| HK2 | 49 | 13 | GLGATTHPTAAVK | 47 |
| CCL19 | 68 | 13 | QLCAPPDQPWVER | 48 |

KLH conjugation was performed as follows. Using the Pierce Imject® Maleimide Activated mcKLH Kit#77611 (Rockford, Ill.), each polypeptide, through the presenting sulfhydryl (—SH) group, was conjugated to the activated mcKLH maleimide group. This provided a hapten to be injected into rabbits to elicit an immune response for the purpose of antibody production. Each of the 39 KLH conjugated polypeptides were sent to Cocalico Biological, Inc. (Reamstown, Pa.) for rabbit antibody production. Each pair of rabbits was injected with two polypeptides. The following protocol was performed:

Day 0=prebleed/initial inoculation
Day 14=polypeptide Boost
Day 21=polypeptide Boost
Day 35=test bleed
Day 49=polypeptide Boost
Day 56=test bleed
Final Boost and production bleed
Final bleed of rabbit CoCalico Biologic returned a pre-injection bleed, plus Day 35 and Day 56 bleeds for each of the 44 polypeptides for antibody titering using an indirect ELISA method. Briefly, each bleed from the rabbit was tested against the two immunogenic polypeptides by an indirect ELISA method. The polypeptide/immunogen was bound to a 96 well plate, and the rabbit antiserum was then added to form a complex. The plate was washed to remove any unbound antibody. Goat anti-rabbit alkaline phosphatase substrate was added, and a color reaction was achieved by the addition of pNPP. The reaction was measured by 405 OD and evaluated for antibody affinity.

Further boosting and production bleeds were collected and titered. The rabbit antisera was then IgG purified by use of a Protein G column purchased from GE Heathcare (Piscataway, N.J.). Each polypeptide was sulfolinked to an affinity column; the corresponding IgG purified rabbit sera was added; and the specific anti-polypeptide antibody was eluted from the column. Briefly, using the Pierce SulfoLink® Immobilization Kit for Peptides #44999, each polypeptide was immobilized through its reduced sulfhydryls to the iodoacetyl groups attached to the coupling resin. To affinity purify the rabbit antibody, the rabbit antiserum was incubated with the first corresponding polypeptide column. The column was then washed, flow through collected, and the purified antibody was eluted off. After a buffer exchange, the polypeptide concentration of the antibody was measured by 280OD. The original flow through collected was then further purified by the second corresponding polypeptide column following the same procedure.

The antibodies were conjugated to Biotin using a kit obtained from Pierce (Rockford, Ill.). Using the Pierce Micro Biotinylation Buffer and Desalting Kit #1860301, the primary amine group from the purified antibody was conjugated to N-Hydroxysuccinimide esters of biotin.

The biotinalyated antibody was bound to strepavidin magnetic bead (Dynabeads® M-280 Strepavidin). The beads were added to the sample to complex with the target polypeptide. The beads were then washed, and the target polypeptide eluted. Table 7 provides a summary of antibodies for the indicated polypeptide markers.

TABLE 7

Summary of antibodies.

| | | | | | Polypeptide fragments | | |
| --- | --- | --- | --- | --- | --- | --- | --- |
| | | | Mass Spec | | # synthesized polypeptide | # tryptic polypeptide fragments | Total # tryptic polypeptide |
| Polypeptide | Antibody production | IHC antibody | serum | tissue | fragments | (10 < size < 25) | fragments |
| ALDH3B2 | Polypeptide fragment injected | | | | 1 | 11 | 30 |
| APOC1 | Commercial Ab available | x | x | | — | 0 | 14 |
| APOF | 1 of 2 Abs obtained | | x | | 2 | 9 | 23 |
| ASPN | 1 of 2 Abs obtained | | | | 2 | 13 | 48 |
| B3GNT6 | Ab obtained | | | | 1 | 6 | 42 |
| C1orf64 | Ab obtained | | | | 1 | 7 | 18 |
| C4A /// C4B | 2 of 3 Abs obtained | x | x | x | 3 | 46 | 176 |
| CCL19 | Kit by R&D System:serum:normal 80% ≦496 pg/mL; PSA 4-10 ng/mL 38% ≧497 pg/mL; PSA 10-1000 ng/mL 27% ≧497 pg/mL | x | | | 0 | 2 | 13 |
| CDH10 | 1 of 2 Abs obtained | | | | 2 | 19 | 75 |
| CDH7 | Ab obtained | | | | 1 | 16 | 72 |
| COL2A1 | 2 of 3 Abs obtained | x | | x | 3 | 44 | 133 |
| COL9A2 | 1 of 3 Abs obtained | | | | 3 | 19 | 60 |
| COMP | Kit by BioVendor: Matching benign and Prostate cancer tissue extracts was tested. Also a small set of de-identified serum samples was analyzed. 1 of 2 Abs obtained. | x | x | | 2 | 22 | 64 |
| CXCL11 | Kit by R&D System serum: normal 80% ≦84 pg/mL; PSA 4-10 ng/mL 13% ≧85 pg/mL; PSA 10-1000 ng/mL 13% ≧85 pg/mL | | | | 0 | 2 | 19 |
| CXCL14 | Kit by R&D System serum: normal 80% ≦445 pg/mL; PSA 4-10 ng/mL 11% ≧446 pg/mL; PSA 10-1000 ng/mL 7% ≧446 pg/mL | x | | | 0 | 1 | 23 |
| CXCL9 | Kit by R&D System serum: normal 80% ≦305 pg/mL; PSA 4-10 ng/mL 50% ≧306 pg/mL; PSA 10-1000 ng/mL 20% ≧306 pg/mL | x | | | 0 | 4 | 30 |
| EFNA4 | Polypeptide fragment injected | x | | | 1 | 5 | 21 |
| F5 | 2 Abs obtained | x | x | | 2 | 62 | 209 |
| FAM77C | Polypeptide fragment injected | | | | 1 | 6 | 29 |
| GPR116 | Polypeptide fragment injected | x | | | 1 | 39 | 103 |
| KAZALD1 | Ab obtained | | | | 1 | 6 | 19 |
| LOC284591 | | | | | — | — | — |
| LOX | 1 of 2 Abs obtained | | | | 2 | 13 | 35 |
| LRRN1 | 2 polypeptide fragments injected | | | | 2 | 20 | 60 |
| LSM14 (FAM61B) | Polypeptide fragment injected | | | | 1 | 8 | 45 |
| MS4A8B | | | | | 0 | 0 | 3 |
| NRN1 | Polypeptide fragment injected | x | | | 1 | 4 | 10 |

TABLE 7-continued

Summary of antibodies.

| Polypeptide | Antibody production | IHC antibody | Mass Spec serum | Mass Spec tissue | # synthesized polypeptide fragments | # tryptic polypeptide fragments (10 < size < 25) | Total # tryptic polypeptide fragments |
|---|---|---|---|---|---|---|---|
| OGDHL | Ab obtained | | | | 1 | 28 | 108 |
| PCDHB10 | Polypeptide fragment injected | | | | 2 | 19 | 65 |
| PCDHGA4 | 2 Abs obtained | | | | 2 | 20 | 73 |
| PCSK6 | 2 polypeptide fragments injected | | | | 2 | 23 | 100 |
| PGLS | Polypeptide fragment injected | | | x | 1 | 8 | 22 |
| RBM35A | Polypeptide fragment injected | | | | 1 | 39 | 113 |
| RP11-35N6.1 (PRG-3) | | | | | 0 | 4 | 8 |
| RPL22L1 | Polypeptide fragment injected | | | | 1 | 26 | 88 |

The antibodies provided herein are used to enrich the corresponding polypeptide markers in serum samples obtained from men with prostate cancer and from controls. The enriched serum samples are then measured on tandem MS/MS.

A total of 39 KLH-conjugated polypeptides were injected into 38 rabbits to immunize them for antibody production. Rabbits were not immunized with the two KLK3 and two HK2 polyp eptide fragments since assays exist for these biomarkers. Each of the 38 rabbits were tittered for the targeted immunogens. Thirty-two polypeptide fragments generated antisera with significant titers (OD450>1.0 at 1/1000 dilution), and further immunization boost is proceeding with the remainder. IgG was purified from the sera from 32 of the 38 rabbits. Greater than 70 µg (average 587 µg; range 77 to 4000 µg) of affinity purified anti-polypeptide fragment antisera was extracted for 27 of the polypeptide fragments. These purified anti-polypeptide fragment antisera were biotinylated for use in affinity extraction of trypsin digested human blood.

Example 3

Mass Spectrometry Measurement Systems

Mass spectrometry measurement systems are designed and used to provide direct MS/MS measurement of trypsin digested fragments for higher concentration polypeptides such as ZAG, Apolipoprotein C1, and Complement C4. For measurement of ZAG, Apolipoprotein C1, and Complement C4, the direct measurement of trypsin digested human serum using a multiple reactions monitoring (MRM) approach of LC-MS/MS was used. The quantitative MS MRM assay approach was used to measure specific polypeptides in complex mixtures such as tryptic digests of plasma. An MS-based approach can provide absolute structural specificity for the polyp eptide, and in combination with appropriate stable isotope-labeled internal standards (SISs), it can provide absolute quantitation of polyp eptide concentration.

The following polypeptides were identified: EIPAWVPEDPAAQITK (SEQ ID NO:49) for ZAG, TPDVSSALDK (SEQ ID NO:50) for APOC1, and TTNIQGINLLFSSR (SEQ ID NO:51) for complement C4. The stable isotope-labeled version of each polypeptide was synthesized and is used to quantitate protein concentration in serum.

Direct MS/MS measurements of trypsin digested polypeptides extracted from prostate tumor tissue and from albumin depleted sera identified polypeptide fragments for the following three biomarkers. In tissue, eight polypeptide fragments of PGLS were detected, one polypeptide fragment of COL 2A1 was detected, and eight polypeptide fragments of Comp C4 were detected. In depleted sera, four polypeptide fragments of APOC1 were detected, five polypeptide fragments of APOF were detected, and eight polypeptide fragments of Comp C4 were detected. Briefly, the samples of tissue extract were prepared by using a standard protocol. For depletion of most abundant proteins from human serum, an "Agilent" column was used that removed albumin, IgG, IgM, haptoglobin, transferrin, and alpha anti-trypsin. The 35-40 µg of total proteins from tissue extract or depleted serum were subjected to SDS-PAGE resolution followed by in-gel trypsin digest and LC-MS/MS analysis.

The polypeptide identification was achieved by nano-flow liquid chromatography electrospray tandem mass spectrometry (nanoLC-ESI-MS/MS) using a ThermoFinnigan LTQ Orbitrap Hybrid Mass Spectrometer (ThermoElectron Bremen, Germany) coupled to an Eksigent nanoLC-2D HPLC system (Eksigent, Dublin, Calif.). The polypeptide mixture was loaded onto a 250 nL OPTI-PAK trap (Optimize Technologies, Oregon City, Oreg.) custom packed with Michrom Magic C8 solid phase (Michrom Bioresources, Auburn, Calif.) and eluted with a 0.2% formic acid/acetonitrile gradient through a Michrom packed tip capillary Magic C18 column (75 µm×150 mm). The LTQ Orbitrap mass spectrometer experiment was set to perform a FT full scan from 380-1600 m/z with resolving power set at 60000 (400 m/z), followed by linear ion trap MS/MS scans on the top 3 ions. Dynamic exclusion was set to 2, and selected ions were placed on an exclusion list for 60 seconds. The MS/MS raw data were converted to DTA files using ThermoElectron Bioworks 3.2 and correlated to theoretical fragmentation patterns of tryptic polypeptide sequences from the Swissprot databases using both SEQUEST™ (ThermoElectron, San Jose, Calif.) and Mascot™ (Matrix Sciences London, UK) search algorithms running on 10 node cluster.

The searches were conducted with fixed cysteine modifications of +57 for carboxamidomethyl-cysteines and variable modifications allowing +16 with methionines for methione sulphoxide, and +42 for protein N-terminal acetylation. The search was restricted to trypsin generated polypeptides allowing for two missed cleavages and was left open to all species. Polypeptide mass search tolerances were set to 10 ppm and fragment mass tolerance were set to ±0.8 Daltons. Polypeptide identifications were considered when both Mascot and Sequest give at least two consensus polypeptides with individual cross correlation or probability scores exceeding a threshold dependent on the precursor charge state, and ranking number one of all the hits for their respective MS/MS spectra.

Analysis of the serum sample PSA1117 MS/MS spectra identified polypeptide fragments from three polypeptides with high confidence. Four polypeptide fragments were identified from the APOC1 encoded polypeptide, five polypeptide fragments were identified from the APOF encoded polypeptide, and 85 polypeptide fragments were identified from the C4 encoded polypeptide. Similar results were obtained from the analysis of serum sample PSA1113, with 79 polypeptide fragments from C4, five polypeptide fragments from APOF, and 15 polypeptide fragments from APOC1.

Example 4

Mass Spectrometry Measurement Systems

Mass spectrometry measurement systems can be designed and used to confirm the predicted trypsin digest patterns for low concentration biomarkers using recombinant polypeptides. Eleven recombinant polypeptides were obtained for confirmation of the predicted trypsin-digested polypeptides (Table 8). 17 polypeptide fragments from these 11 biomarkers were confirmed to generate strong MS/MS signals (Table 8). Briefly, a standard protocol was used to obtain a tryptic digest in solution. In particular, from 1 μg to 25 μg of protein was denatured by 6M urea and then reduced and alkylated. The ratio of trypsin to protein was 1:50.

LC-MS/MS data were collected both on a Q-TOF Premier quadrapole time-of-flight mass spectrometer (Waters Corp., Milford, Mass.) and an API 5000 triple quadrapole mass spectrometer (Applied Biosystems, Foster City, Calif.). Full scan LC-MS/MS data was acquired on the Q-TOF Premier to identify tryptic fragments and their MS/MS product ions produced from the digestion of the recombinant polypeptides. The instrument was set up to perform a data dependent analysis experiment where precursor ions are selected for MS/MS analysis by the acquisition software. The identified polypeptide fragments exhibiting the best signal intensity and chromatographic peak shape for a given parent polypeptide were selected. The results of these experiments are presented in Table 8. Fragment ions from these polypeptides were used to develop LC-MS/MS instrument conditions on the API 5000.

TABLE 8

Tryptic polypeptide fragments and MRM transitions for available recombinant polypeptides.

| Polypeptide | Polypeptide fragment | SEQ ID NO: | MRM Transitions |
|---|---|---|---|
| Zinc-alpha-2-glycoprotein (ZAG) | EIPAWVPFDPAAQITK | 52 | 891.9/1087.7 |
| PGLS | ILEDQEENPLPAALVQPHTGK | 28 | $767.07^{3+}$/1118.5 |
|  | ELPAAVAPAGPASLAR | 53 | 839/1489 |
| ADAMTS8 | PLPEPLTVQLLTVPGEVFPPK | 54 | $757.77^{3+}$/870.3 |
| ALDH3B2 | VAIGGQSNESDR | 55 | $616.8^{2+}$/949.4 |
|  | LLPALQSTITR | 56 | $606.8^{2+}$/493.9 |
| APOF | QGGVNATQVLIQHLR | 57 | $817.46^{2+}$/553.4 |
|  | SGVQQLIQYYQDQK | 16 | $819.4^{+2}$/972.2 |
| GJB1 | LEGHGDPLHEEVK | 58 | $786.9^{+2}$/964.5 |
| PCDHB10 | DLGLAEGELAAR | 59 | $607.8^{+2}$/816.4 |
|  | QYLLLDSHTGNLLTNEK | 26 | $980^{+2}$/1213.4 |
| CDH7 | SILQGQPYFSVEPK | 60 | $652.02^{+3}$/966.4 |
|  | FLSLGPFSDTTTVK | 61 | $756.9^{+2}$/995.4 |
|  | SILQGQPYFSVEPK | 60 | $796.92^{+2}$/966.4 |
| PLA2G7 | IAVIGHSFGGATVIQTLSEDQR | 62 | $1150^{+2}$/1089.4 |
| Apolipoprotein C-I | TPDVSSALDK | 50 | 516.8/620.3 |

TABLE 8-continued

Tryptic polypeptide fragments and MRM transitions for available recombinant polypeptides.

| Polypeptide | Polypeptide fragment | SEQ ID NO: | MRM Transitions |
|---|---|---|---|
| Complement C4 | TTNIQGINLLFSSR | 51 | $782.4^{+2}/1006.5$ |
|  | VGDTLNLNLR | 63 | $557.8^{+2}/629.3$ |

Example 5

Immunohistochemistry Staining of Prostate Tissue Sections

Immunohistochemistry (IHC) staining of prostate tissue sections is used to confirm the tissue presence of the biomarkers such as those having commercially available antisera. IHC targeted antisera was obtained for three biomarkers. In addition, a panel of tissues was identified from patients with prostate cancer that can be used to evaluate the quantity and location of IHC activity associated with polypeptide markers.

The IHC protocols were developed and performed in Mayo Foundation Tissue and Cell Molecular Analysis (TACMA) Laboratory. Formalin-fixed, paraffin-embedded (FFPE) samples were deparaffinized with three changes of xylene and rehydrated in a series of ethanols (100%, 95%, 70% EtOH) and rinsed in distilled water. Slides were placed in a preheated 1 mM EDTA, pH 8.0 retrieval buffer for 30 minutes then cooled in the buffer for 5 minutes followed by a 5 minute rinse in running distilled water. After the heat inactivated epitope retrieval step, slides were placed on the DAKO Autostainer for the following procedure. Sections were incubated with 3% $H_2O_2$ in ethanol for 5 minutes to inactivate the endogenous peroxides. Serum free blocking reagent, (DAKO), was added to slides for 5 minutes. The sections were incubated with specific antibodies. Sections were rinsed with TBST wash buffer. Labeled polymer EnVision+Dual Link System/HRP (DAKO #K4061, Carpenteria, Calif.) was incubated for 15 minutes. The slides were rinsed with TBST wash buffer, and incubated in diaminobenzidine (DAB+) for 10 minutes, counterstained with Modified Schmidts' Hematoxylin for 5 minutes followed by a 3 minute tap water rinse, and mounted with an aqueous mounting media.

The main protocol was used with minor modification for each polypeptide.

Ephrin A4 IHC: The sections were incubated in rabbit anti-human Ephrin A4 polyclonal Abs at 1:100 dilution (catalog#: ab28385; Abcam, Cambridge, Mass.) for 60 minutes.

F5 IHC: The sections were incubated in rabbit anti-human F5 polyclonal Abs at 1:500 dilution (catalog#: HPA002036; Atlas Antibodies, Stockholm, Sweden) overnight at room temperature.

Procollagen Type IIA (Col2A) IHC: The sections were incubated in rabbit anti-human Procollagen type IIA polyclonal Abs at 1:500 dilution (catalog#ab17771, Abcam, Cambridge, Mass.) for 60 minutes.

Results

Twenty cases were stained and evaluated for staining intensity of the prostate tumor and benign prostate tissue. Sections were scored using an ordinal scale of 0-3, with 0 representing no staining, 1 weak staining, 2 moderate staining, and 3 heavy staining. Based on the analysis (Table 9), F5 was more expressed in 30% (6 of 20) of the prostate cancer cases, COL2A was more expressed in 80% (16 of 20) of the prostate cancer cases, and Ephrin A4 was more expressed in 60% (12 of 20) prostate cancer cases.

TABLE 9

IHC staining summary for F5, COL2A, and Ephrin A4.

| Block # | GS | Cancer F5 | Benign F5 | Cancer CD12A | Benign CD12A | Cancer Ephrin A4 | Benign Ephrin A4 |
|---|---|---|---|---|---|---|---|
| 1 | 6 | 1 | 1 | 3 | 3 | 1 | 1 |
| 2 | 7 | 1 | 0 | 3 | 2 | 2 | 1 |
| 3 | 6 | 2 | 1 | 3 | 1 | 2 | 1 |
| 4 | 6 | 2 | 0 | 3 | 1 | 2 | 1 |
| 5 | 6 | 0 | 0 | 3 | 2 | 1 | 0 |
| 6 | 7 | 0 | 1 | 3 | 2 | 1 | 0 |
| 7 | 8 | 0 | 1 | 2 | 1 | 1 | 1 |
| 8 | 9 | 0 | 0 | 3 | 1 | 1 | 1 |
| 9 | 7 | 1 | 0 | 3 | 2 | 2 | 1 |
| 10 | 6 | 0 | 1 | 1 | 1 | 0 | 0 |
| 11 | 6 | 0 | 1 | 2 | 1 | 0 | 0 |
| 12 | 6 | 1 | 1 | 1 | 1 | 1 | 0 |
| 13 | 7 | 3 | 1 | 3 | 2 | 3 | NA |
| 14 | 7 | 3 | 1 | 3 | 1 | 2 | 0 |
| 15 | 8 | 2 | 1 | 3 | 2 | 2 | 1 |
| 16 | 10 | 0 | 1 | 3 | 1 | 2 | 1 |
| 17 | 7 | 0 | 0 | 3 | 2 | 1 | 2 |
| 18 | 10 | 1 | NA | 3 | NA | 1 | NA |
| 19 | 6 | 1 | 1 | 2 | 1 | 1 | 0 |
| 20 | 7 | 3 | 1 | 3 | 1 | 2 | 1 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An enzyme-linked immunosorbent assay method for identifying a male human as having prostate cancer, said method comprising:
   (a) obtaining a serum sample of a male human,
   (b) performing an enzyme-linked immunosorbent assay to detect the presence of an elevated level of a polypeptide encoded by an F5 or COL2A1 nucleic acid within said sample, and
   (c) classifying said male human as having prostate cancer based at least in part on said presence.

2. The method of claim 1, wherein said polypeptide is a polypeptide encoded by said F5 nucleic acid.

3. The method of claim 1, wherein said polypeptide is a polypeptide encoded by said COL2A1 nucleic acid.

* * * * *

UNITED STATES PATENT AND TRADEMARK OFFICE
CERTIFICATE OF CORRECTION

PATENT NO. : 8,273,539 B2  
APPLICATION NO. : 12/442685  
DATED : September 25, 2012  
INVENTOR(S) : Klee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 414 days.

Signed and Sealed this
Nineteenth Day of August, 2014

Michelle K. Lee
*Deputy Director of the United States Patent and Trademark Office*